United States Patent
Mifune et al.

[11] Patent Number: 5,807,092
[45] Date of Patent: Sep. 15, 1998

[54] METHOD OF AND DEVICE FOR DETECTING THE RESIDUAL OF GAS QUANTITY IN A CASSETTE-TYPE GAS CYLINDER

[75] Inventors: Hideo Mifune; Yasuaki Nakamura, both of Shizuoka-ken, Japan

[73] Assignee: Tokai Corporation, Kanagawa-ken, Japan

[21] Appl. No.: 628,673
[22] PCT Filed: Aug. 1, 1995
[86] PCT No.: PCT/JP95/01524
§ 371 Date: Apr. 2, 1996
§ 102(e) Date: Apr. 2, 1996
[87] PCT Pub. No.: WO96/04512
PCT Pub. Date: Feb. 15, 1996

[30] Foreign Application Priority Data

Aug. 3, 1994 [JP] Japan .................................... 6-182142

[51] Int. Cl.[6] ...................................................... F23D 5/12
[52] U.S. Cl. ............................... 431/13; 126/44; 126/52; 126/39 R; 126/275 R; 126/273 R; 73/149
[58] Field of Search ............................... 431/13; 73/149, 73/143; 126/39 R, 44, 275 R, 273 R, 52

[56] References Cited

U.S. PATENT DOCUMENTS

| 4,599,892 | 7/1986 | Doshi ......................................... 73/49.2 |
|---|---|---|
| 4,811,595 | 3/1989 | Marciniak et al. ........................ 73/149 |
| 4,949,584 | 8/1990 | Lade et al. .............................. 73/149 X |
| 4,991,433 | 2/1991 | Warnaka et al. ....................... 73/149 X |
| 5,385,069 | 1/1995 | Johnson, Jr. ........................... 73/149 X |
| 5,612,622 | 3/1997 | Goldman et al. ........................ 324/444 |

FOREIGN PATENT DOCUMENTS

| 50-132960 | 10/1975 | Japan . |
|---|---|---|
| 3-76129 | 7/1991 | Japan . |

*Primary Examiner*—Larry Jones
*Attorney, Agent, or Firm*—Baker & Botts, L.L.P.

[57] ABSTRACT

A gas cylinder joined to a gas appliance. Based on the knowledge that a resonance frequency of cassette type gas cylinder does not vary with a residual quantity of gas therein a transmitter and a receiver are placed in positions opposed to a weld zone of the trunk portion of the gas cylinder and which permits an output voltage of the receiver with respect to a residual quantity of the gas to be detected at a specific resonance frequency of the gas cylinder. The resonance frequency is not lower than a predetermined level, the residual quantity of a liquefied gas in the cylinder being detected by transmitting the specific resonance frequency signal from the transmitter and detecting a reception output of not lower than a predetermined level by the receiver. This enables a residual quantity of the gas in the liquefied gas containing cassette type gas cylinder to be detected reliably from the outside.

15 Claims, 17 Drawing Sheets

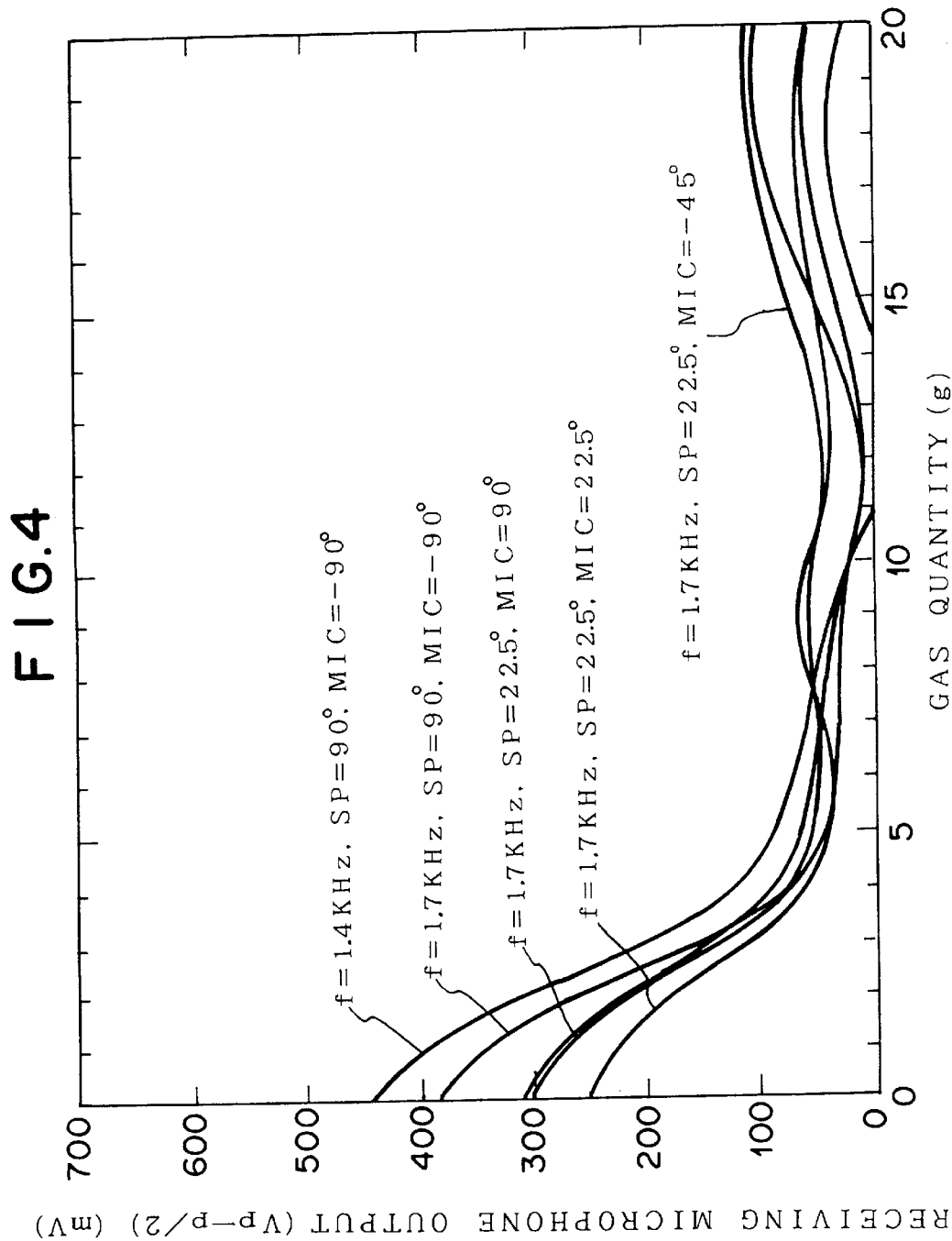

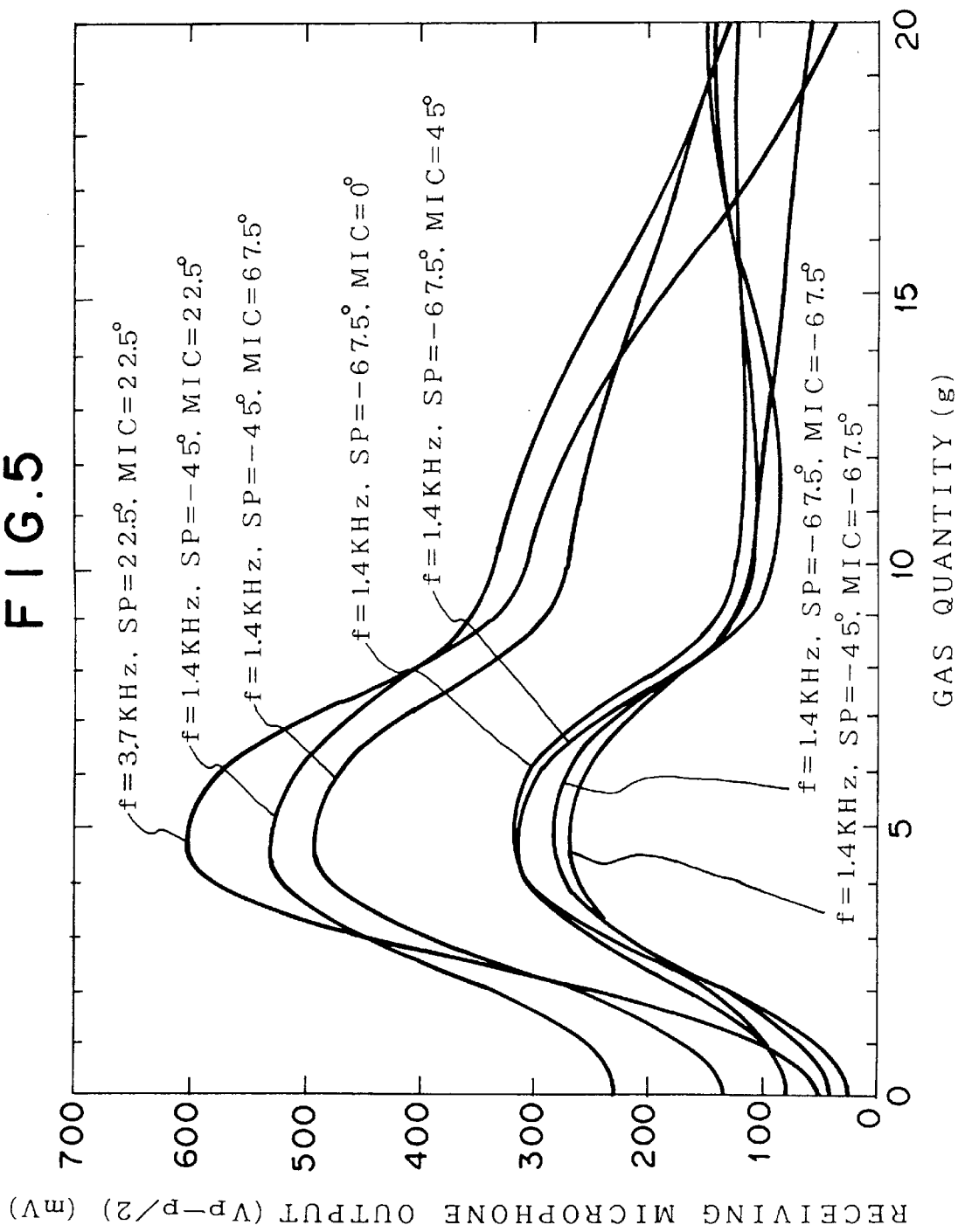

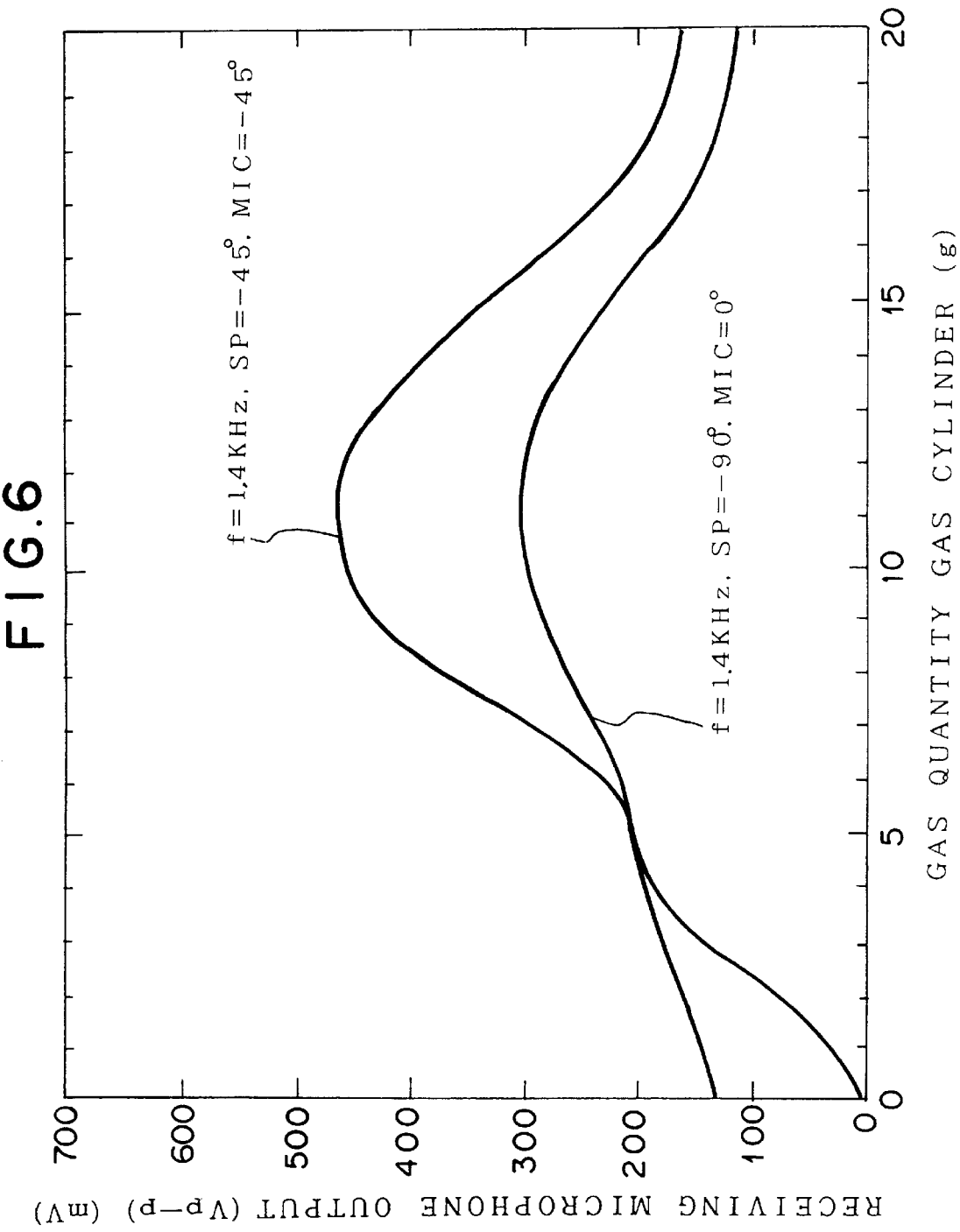

(TRANSMITTING SPEAKER POSITION=0°, RECEIVING MICROPHONE POSITION=45°)

RECEIVING MICROPHONE OUTPUT (Vp-p/2, mV), GAS
QUANTITY=10g, OSCILLATION FREQUENCY=1.4KHz

RECEIVING MICROPHONE OUTPUT (Vp-p/2, mV), GAS
QUANTITY=20g, OSCILLATION FREQUENCY=1.4KHz

RECEIVING MICROPHONE OUTPUT (Vp-p/2, mV), GAS QUANTITY=0g, OSCILLATION FREQUENCY=1.7KHz

RECEIVING MICROPHONE OUTPUT (Vp-p/2, mV), GAS QUANTITY=5g, OSCILLATION FREQUENCY=1.7KHz

RECEIVING MICROPHONE OUTPUT (Vp-p/2, mV) 、GAS QUANTITY=10g、OSCILLATION FREQUENCY=1.7KHz

RECEIVING MICROPHONE OUTPUT (Vp-p/2, mV) 、GAS QUANTITY=20g、OSCILLATION FREQUENCY=1.7KHz

RECEIVING MICROPHONE OUTPUT (Vp-p/2, mV), GAS QUANTITY=0g, OSCILLATION FREQUENCY=2.2KHz

RECEIVING MICROPHONE OUTPUT (Vp-p/2, mV), GAS QUANTITY=5g, OSCILLATION FREQUENCY=2.2KHz

RECEIVING MICROPHONE OUTPUT (Vp-p/2, mV), GAS QUANTITY=10g, OSCILLATION FREQUENCY=2.2KHz

RECEIVING MICROPHONE OUTPUT (Vp-p/2, mV), GAS QUANTITY=20g, OSCILLATION FREQUENCY=2.2KHz

RESONANT FREQUENCY=1.4KHz

RECEIVING MICROPHONE OUTPUT (Vp-p/2) (mV)
TRANSMITTING SPEAKER POSITION (°) -45.0°

RESONANT FREQUENCY=1.4KHz

RECEIVING MICROPHONE OUTPUT (Vp-p/2) (mV)
TRANSMITTING SPEAKER POSITION (°) -67.5°

METHOD OF AND DEVICE FOR DETECTING THE RESIDUAL OF GAS QUANTITY IN A CASSETTE-TYPE GAS CYLINDER

SPECIFICATION

The present invention relates to a method of detecting the residual quantity in a cassette-type gas cylinder and to a device therefor which are so devised that when a cassette-type gas cylinder containing liquefied gas fuel is set in a gas appliance such as a portable gas stove, etc. the amount of liquefied gas, which falls accompanying use, is detected at a specific residual gas quantity.

BACKGROUND TECHNOLOGY

Devices in which, instead of gas being supplied from a city gas outlet by a gas hose, a cassette-type gas cylinder in which liquefied gas fuel is contained in a container is set in a table-top gas range, etc. and combustion is effected through supply of gas from this gas cylinder are known conventionally. Such a cassette-type gas cylinder is also used in various other types of gas apparatus such as portable ranges or stoves for use outdoors.

In a gas appliance using a cassette-type gas cylinder, if the arrangement is made such that the amount of gas remaining in the gas cylinder can be detected by means of the apparatus, it is easy to respond when the gas is used up. If the amount of gas remaining is not known, there are problems in connection with safety and with waste disposal, since the gas cylinder may be replaced or thrown away while there is still gas remaining in it.

By way of a method for detecting the amount of gas remaining in such a gas cylinder, there is known a method in which changes in the weight of a gas cylinder are detected (see Japanese Laid-open Patent Application Nos. 4-270811 and 5-203143, etc.), a method in which the gas pressure is detected (see Japanese Laid-open Utility Model Application No. 62-97399) and a method in which the combustion time is detected (see Japanese Laid-open Utility Model Application No. 5-8243). However, with these arrangements, accurate, stable detection of very small residual quantities is difficult, and complex and expensive mechanisms and control systems are needed in order to improve the detection precision.

Further, by way of methods for detecting the liquid level in a bottle, tank or high-pressure cylinder, etc. containing a liquid, a variety of techniques which use the resonance of such a container or the cavity resonance of the container's interior have been proposed (see Japanese Laid-open Utility Model Application No. 3-76129 and Japanese Laid-open Patent Application Nos. 5-223612 and 50-132960).

Specifically, there is disclosed a method in which a container's resonant frequency when the liquid surface comes to a specific position inside the container is determined, sound waves of this frequency are produced, and the liquid level is detected at the point when the container resonates. This method is one which uses the cavity resonance of a container and in which the liquid level is detected through the container's resonant sound, taking advantage of the characteristic that, when the liquid level falls and the cavity inside the container becomes larger, this is accompanied by a shift in the resonant frequency to a lower frequency.

However, this method of using a container's cavity resonance sound to detect the liquid level cannot be used directly for the detection of the residual liquid gas quantity in a cassette-type gas cylinder.

That is, in the abovedescribed prior art technique, the shape and structure of the container are simple and the container is one in which, whether there are joint portions or not, there are homogeneous joints, and its resonance and the resonance of the cavity portion in it in which contents are held are simple and display a clear resonance mode, and the technique is one which is based on the characteristic that the resonant frequency changes in accordance with the amount of material contained and which detects a residual quantity simply from the container's resonant sound. Also, setting to any detection liquid level can be made by altering the resonant frequency that is transmitted.

In contrast, as shown in FIG. 2, in the can structure of a cassette-type gas cylinder, the can body 2 of a gas cylinder 1 is an element in which a steel sheet is rolled round and a butt weld portion 2a is electrically welded, a bottom plate 3 pressed to a hemispherical shape and a cover portion 4 are crimp-bonded to opposite ends of this cylindrical can body 2, and a mounting cap 6 incorporating a valve 5 which opens and closes spray-out of liquefied gas fuel is fixed to the cover portion 4. The gas passage leading to the valve 5 is defined by an L-shaped housing 7, and the inner-end opening of this L-shaped housing 7 is disposed near the wall surface of the can body 2. A cut-in recess portion 6a is formed in the mounting cap 6 in correspondence to the bend direction of the L-shaped housing 7. 5a is a gasket, 5b is a spring, and 8 is a cap gasket.

The above cassette-type gas cylinder 1 is laid horizontally and is set in a gas appliance in a manner such that the cut-in recess portion 6a is located at the top. This is a structure which is made such that there is always spray-out of vaporized gas from the gas space in the gas cylinder 1, and fuel is never supplied while still in a liquefied state. In this case, the setting is such that the weld portion 2a of the can body 2 is also in a set position, specifically, in a bottom location shifted about 20° from the vertical.

It has been ascertained that the resonance modes of a gas cylinder 1 with a structure such as above are extremely complex, and that the characteristic is not one such that the resonant frequency changes simply in accordance with residual quantity liquefied gas fuel.

That is, accompanying use of the gas appliance, the level of the liquefied gas contained in the cassette-type gas cylinder 1 falls, and the surface of the liquid comes to contact the can body 2 at the locations indicated by 20 g, 10 g and 5 g in FIG. 3. The gas cylinder 1 is made of thin steel sheet (0.2 mm thick), and so for resonance when the gas cylinder 1 is empty, a vibration mode is formed at the weld portion 2a, since this weld portion 2a is strong, and, together with this, complex resonance is displayed at symmetrical locations centering on the position (0°) opposite the weld portion 2a of the can body 2. Further, since the gas cylinder 1 is light and the metal sheet is thin, the effect of the liquid level on the resonance of the gas cylinder 1 when there is liquefied gas in it is great, and it was found that when the level of the liquefied gas is low, the effect appears still more strongly and the vibration of different portions of the can body becomes still more complex (see FIGS. 8–10, which are described below).

For the detection of the liquid level in a cassette-type gas cylinder, therefore, it is impossible to effect detection by the conventionally known procedure using simple resonant sound at a resonant frequency of a container. With regard to resonance waveform frequency analysis too, since this varies depending on the positions of the transmitting speaker and the resonance receiving microphone, and since the situation is completely different from that when the container shape is simple and similar frequency analysis waveforms are obtained whatever the measurement conditions are, this method cannot be used for detection of the residual quantity in a cassette-type gas cylinder.

Generally, if a container performs simple vibration, it is possible to determine the liquid level by detecting the resonant frequency if there is a correlation between the liquid level and the resonant frequency in a single vibration mode, or the liquid level can be determined by frequency analysis waveform measurements if there is a correlation between the liquid level and the frequency analysis waveforms of resonant frequencies in a number of vibration modes. However, in the case of a container such as a cassette-type gas cylinder in which a cylinder constituted by welding a thin steel sheet is used as a can body and its opposite ends are shrunk-fixed to a hemispherical bottom plate and a cover, the weld portion and the fixed portions at the two ends are strong and greatly restrain vibration of the container, and so vibration in the form of simple movement is not performed.

Further, since the container is constituted by a thin steel sheet, when liquefied gas is present in it, its resonance is greatly affected by the liquefied gas but it has been found that changes in this case are not related to the amount of liquefied gas. Although, in the case of a container which performs simple vibration such as described above, changes in vibration that are in a correlation with the amount of material contained are brought about, with a cassette-type gas cylinder there is complex resonance, and no changes in the resonant frequency in correlation to the residual amount of liquefied gas were observed.

In view of the above situation, it is the object of the present invention to provide a cassette-type gas cylinder residual quantity detection method and residual quantity detection device which, by using resonant frequencies, make it possible to detect, from the exterior, when the remaining amount of internal liquefied gas reaches a set state, even if the cassette-type gas cylinder is one with which there are complex resonance modes.

DISCLOSURE OF THE INVENTION

Basically, the cassette-type gas cylinder residual quantity detection method of the invention, which resolves the problem described above, has been devised as the result of it having been noted that, in a cassette-type gas cylinder with a structure such as described above, the resonant frequency does not change depending on the residual amount of gas, and the method is one in which a gas cylinder containing liquefied gas is set in a gas appliance, a transmitter which excites the gas cylinder and a receiver which detects vibration of the gas cylinder are installed in positions for each of which the position that is opposite the weld portion of the can body of the gas cylinder is taken as a reference, and at which, when there is a specific resonant frequency and a residual gas quantity it is intended to detect, the reception output of the receiver becomes greater than a set value, the transmitter transmits signals of the abovenoted specific resonant frequency, and the time when the reception output of the receiver becomes more than the set value is detected as indicating that the amount of liquefied gas in the gas cylinder is the abovenoted residual gas quantity.

Specifically, for the installation positions of the abovenoted transmitter and receiver and the setting of resonant frequencies, a cassette-type gas cylinder containing liquefied gas is set in a gas appliance, and, in this state, the transmitter, which excites the gas cylinder, and the receiver, which detects vibration of the gas cylinder, are installed near the can body of the gas cylinder, the frequency of excitation signals transmitted by the transmitter is varied and the resonant frequencies that are produced in the gas cylinder without relation to the amount of liquefied gas in the gas cylinder are determined and, taking as a reference the position that is opposite the weld portion of the can body of the gas cylinder, the relations of the transmitter and receiver dispositions and the reception outputs in respect of the amount of liquefied gas in the gas cylinder at the resonant frequencies are determined, and these relations are used to determine the installation positions of the transmitter and receiver at which, when there is a specific residual amount of gas which it is wished to detect, the reception output produced by the receiver becomes more than a set value.

Preferably, the frequency of the excitation signals produced by the transmitter is set at 1.3–1.5 kHz, 1.6–1.8 kHz, 2.1–2.3 kHz or 3.6–3.8 kHz. It is also possible to transmit, from the transmitter, signals in which there is superimposed addition of plural resonant frequencies at which the reception output becomes more than a set value when there is a specific residual gas quantity, and to detect that the amount of liquefied gas is the specific residual gas quantity when the reception output becomes greater than the set value at each resonant frequency. Further, if transmitter and receiver installation positions and resonant frequencies with the characteristics that the reception output increases to above the set value at plural residual gas quantities are set, it is possible to detect plural residual gas quantities.

The cassette-type gas cylinder residual quantity detection apparatus of the invention is one in which a cassette-type gas cylinder containing liquefied gas is set in a gas appliance, a transmitter which excites the gas cylinder and a receiver which detects gas cylinder vibration are installed near the can body of the gas cylinder in positions for each of which the position that is opposite the weld portion of the can body is taken as a reference, and at which the reception output of the receiver becomes greater than a set value when there is a specific resonant frequency and a residual gas quantity it is wished to detect, an oscillation circuit which produces signals of a specific resonant frequency is connected to the transmitter, and a monitor circuit which detects that the reception output at the above reception frequency is greater than a set value is connected to the receiver.

Another cassette-type gas cylinder residual quantity detection apparatus of the invention is one in which a cassette-type gas cylinder containing liquefied gas is set in a gas appliance, a transmitter which excites the gas cylinder and a receiver which detects gas cylinder vibration are installed in positions for each of which the position that is opposite the weld portion of the can body is taken as a reference, and at which the reception output of the receiver becomes greater than a set value when there is a specific resonant frequency and a residual gas quantity it is wished to detect, an oscillation circuit which produces specific resonant frequency signals is connected to the transmitter, a monitor circuit which detects that the reception output at the above reception frequency is greater than a set value is connected to the receiver, and there is also connected a feedback circuit which feeds back a portion of the resonant frequency reception signals to the transmission circuit.

A device which is constituted by a transmitting speaker and which excites a gas cylinder with sound pressure, or a device which is constituted by a transmitting coil and with which a gas cylinder can body constituted by a magnetic body is excited by imposition of an alternating magnetic field produced by the transmitting coil, or a device which is constituted by an electromagnetic drive vibrator or a piezo-electric element, etc. and whose vibration excites a can body, etc. can be used as the transmitter. An arrangement in which the transmitter is constituted by a transmitting coil and the receiver is constituted by a receiving microphone is particularly suitable.

Basically, in the cassette-type gas cylinder residual quantity detection method according to the invention the system is based on the characteristic that, as the result of setting a resonant frequency and setting the installation positions of a transmitter and a receiver, the reception output becomes more than a set value when there is a specific amount of gas remaining, and if the amount of fuel contained in a container is more than the residual gas quantity it is required to detect, even if the gas cylinder is excited by resonance frequency signals from the transmitter, the degree of resonance is small and the resonance frequency reception output at the receiver is low, and, in this state, the reception output does not become greater than the set value and it is not judged that the remaining amount of liquefied gas is such that the specific liquid level has been reached. On the other hand, when the remaining amount of liquefied gas reaches the set amount, the degree of resonance at the resonant frequency transmitted from the transmitter becomes large, the reception output at the resonant frequency received by the receiver becomes large, and since, as a result of this output exceeding the set value, it is detected that there is a fall to the set gas residual quantity, the specific residual gas quantity can be detected precisely, and it is possible to prevent the occurrence of fuel run-out at an unexpected time, even in the case of a cassette-type gas cylinder with complex vibration modes.

The resonant frequency and the transmitter and receiver installation positions corresponding to the residual gas quantity it is required to detect at a resonant frequency are set by determining resonant frequencies that are produced regardless of the amount of liquefied gas that is contained, determining the relations between the transmitter and receiver positions and the reception outputs corresponding to the amounts of liquefied gas at these resonant frequencies, and determining from these relations the transmitter and receiver installation positions with which the reception output produced by the receiver will become greater than a set value when there is a specific residual gas quantity it is required to detect, and residual quantity detection can be effected by finding the optimum installation positions.

In a separately excited residual quantity detection apparatus-in which the transmitter and receiver are set in the positions at which the reception output produced at a resonant frequency by the receiver in correspondence to the amount of liquefied gas remaining in the gas cylinder becomes greater than the set value, an oscillation circuit which produces specific resonant frequency signals is connected to the transmitter, and a monitor circuit which detects when the reception output at the above resonant frequency is greater than a set value is connected to the receiver, detection and notification around the time a specific residual quantity is reached are effected, and this residual quantity detection is effected with a simple circuit configuration.

Further, with a self-excitation type residual quantity detection apparatus in which the transmitter and receiver are set in positions at which the reception output produced at a resonant frequency by the receiver in correspondence to the amount of liquefied gas remaining in a gas cylinder becomes greater than a set value, an oscillation circuit is connected to the transmitter, a monitor circuit which detects that the resonant frequency reception output is greater than the set value is connected to the receiver, and a feedback circuit which feeds back a portion of the resonant frequency reception signals to the transmission circuit is connected, it is possible to accurately detect a state in which the set residual gas quantity is reached even if the excitation signals produced by the transmitter are weak.

A transmitting speaker, a transmitting coil or a vibration, etc. can be used for the transmitter, and a receiving microphone, a receiving coil or a pickup, etc. can be used for the receiver, and constituting the transmitter by a transmission coil and the receiver by a receiving microphone is particularly suitable, since the can body of the gas cylinder is excited in a no-contact manner, signals are not input directly to the receiver from the transmitter, and it is difficult for incorrect operation to occur.

According to the invention described above, a cassette-type gas cylinder is set in a gas apparatus, and, taking the position that is opposite the weld portion of the body of the cylinder can as a reference, the transmitter and the receiver are set in positions at which the reception output of the receiver becomes more than a set value when there is a specific resonant frequency of the cylinder can and a residual gas quantity it is required to detect, signals of this specific resonant frequency are transmitted by the transmitter, and the abovenoted residual gas quantity is detected through detection of the reception output at the receiver, whereby, even in a cassette-type gas cylinder with which the resonant frequency does not change depending on the amount of liquefied gas contained, by suitable positioning of the transmitter and receiver and selection of the resonant frequency, it is possible to detect the residual quantity from the exterior, without installing a detection device inside the gas cylinder, and it is therefore possible to prevent the occurrence of fuel run-out at an unexpected time. This operation can be performed by means of a comparatively simple circuit configuration, precision in detection can be achieved without using a device with high measurement precision, and it is possible to ensure high reliability.

BRIEF DESCRIPTION OF THE DRAWINGS

FIG. 4 to FIG. 6 are characteristic plots showing the relations between the amounts of gas in a cassette-type gas cylinder and receiving microphone outputs in various detection conditions.

DESCRIPTION OF MODE OF PRACTICE OF THE INVENTION

Examples of the invention will now be described with reference to the drawings.

EXAMPLE 1

Figure 1:
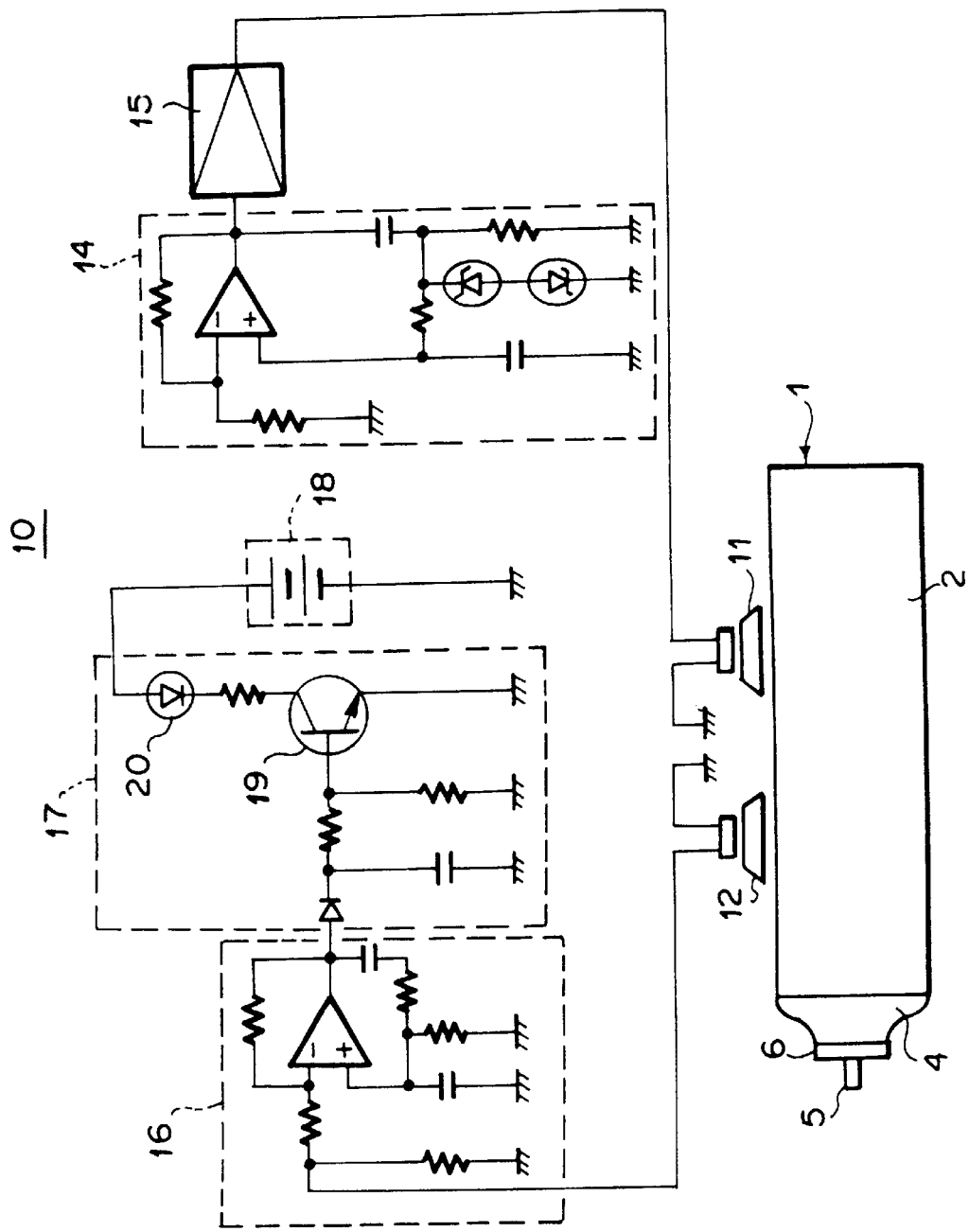
FIG. 1 is a circuit diagram showing the general configuration of a cassette-type gas cylinder residual quantity detection apparatus in one example of practice of the invention.

FIG. 1 shows the general configuration of the apparatus for practising the cassette-type gas cylinder residual quantity detection method in this example.

Figure 2:
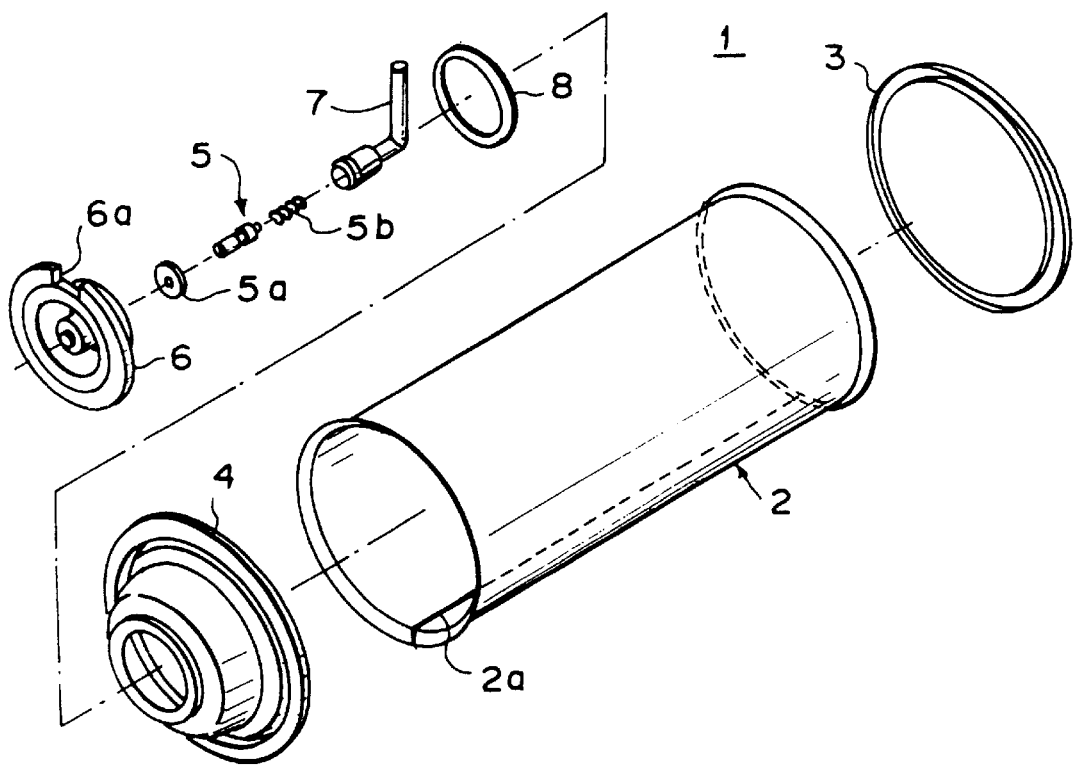
FIG. 2 is a disassembly perspective view of a cassette-type gas cylinder.

A gas cylinder 1 is constituted by a can body 2, a bottom plate 3, a cover portion 4 and a valve 5, etc., as shown in FIG. 2, and it is set horizontally in a gas appliance not shown.

The residual quantity detection apparatus 10 is also installed in this gas apparatus, and it is provided with a transmitter 11 which is positioned near the can body of the gas cylinder 1 and excites the gas cylinder 1 and with a receiver 12 which detects vibration of the gas cylinder 1. In practice, the transmitter 11 and the receiver 12 are installed at approximately the centre in the direction of length of the gas cylinder 1 and at set angular positions going peripherally, the transmitter 11 being set at the 90° position and the receiver at the −90° position in the example of FIG. 3.

Figure 3:
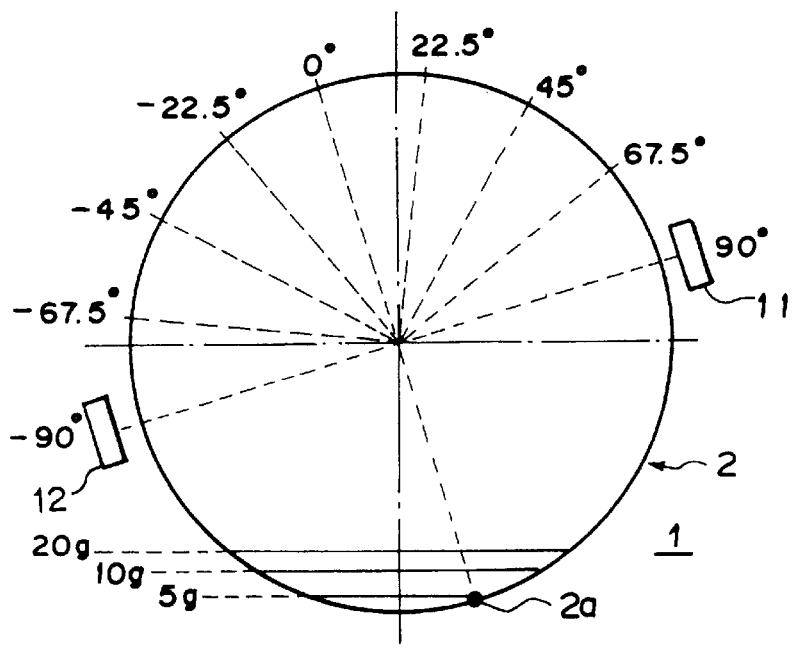
FIG. 3 is an explanatory drawing showing an example of positioning of a transmitter and a receiver in the residual quantity detection apparatus of FIG. 1 relative to a cassette-type gas cylinder.

The installation example of FIG. 3 is a case in which the residual quantity is detected when the amount of remaining liquefied gas contained in the gas cylinder 1 is close to 0 g (when it is, eg, 2 g). The transmitter 11 and receiver 12 installation angles are represented as a positive angle on the right and a negative angle on the left, taking as the reference point 0° the 180° position facing the weld portion 2a of the can body 2 of the gas cylinder 1.

The transmitter 11 is constituted by a transmitting speaker, and oscillation signals from an oscillation circuit 14 are input into the transmitter 11 via an amplifier 15 and excite the can body 2 of the gas cylinder 1. The receiver 2 is constituted by a receiving microphone, and reception output detected by the receiver 12 is input into a monitor circuit 17 via a bandpass filter 16.

The oscillation circuit 14 is a unit which, when it excites the gas cylinder 1 at a specific resonant frequency, its oscillation frequency is made coincident with the resonant frequency, and when a resonant frequency is selected at the detection end, it outputs broadband oscillation signals. The bandpass filter 16 is so set that it sends the resonant frequency output signals to the monitor circuit 17, and the monitor circuit 17 has a light-emitting diode 20 as a display.

With the abovedescribed configuration, signals from the oscillation circuit 14 are input into the transmitter 11 via the amplifier 15 and excite the gas cylinder 1, signals detected by the receiver 12 go via the bandpass filter 16, which is for the purpose of further ensuring proper performance, reception output consisting of a specific frequency component is input into a transistor 19 of the monitor circuit 17, the transistor 19 is driven in accordance with the voltage of this output, and the light-emitting diode 20 is caused to emit light by a power supply 18.

Around the time that the liquefied gas residual quantity reaches a set value, the resonance of the gas cylinder 1 increases and the voltage of the reception output from the receiver 12 becomes more than a set value. Accompanying this, when the output voltage exceeds the set value, the amount of light emitted by the light-emitting diode 20 gradually increases, from about the time of the residual gas quantity it is wished to detect is reached, and it reaches a maximum at the resonance point. The emission of light by this light-emitting diode 20 and the light quantity make it possible to detect that the specific residual quantity of liquefied gas has been reached.

Examples of the relations between liquefied gas residual quantity it is wished to detect and the resonant frequency values and the transmitter 11 and receiver 12 installation positions are shown in Table 1.

TABLE 1

| GAS RESIDUAL QUANTITY TO BE DETECTED | RESONANT | TRANSMITTER | RECEIVER |
|---|---|---|---|
| 0 g | 1.4 kHz | 90° | −90° |
| 0 g | 1.7 kHz | 90° | −90° |
| 0 g | 1.7 kHz | 22.5° | 90° |
| 0 g | 1.7 kHz | 22.5° | 22.5° |
| 0 g | 1.7 kHz | 22.5° | −45° |
| 5 g | 1.4 kHz | −45° | 22.5° |
| 5 g | 1.4 kHz | −45° | 67.5° |
| 5 g | 1.4 kHz | −67.5° | 0° |
| 5 g | 1.4 kHz | −67.5° | 45° |
| 5 g | 1.4 kHz | −67.5° | −67.5° |
| 5 g | 1.4 kHz | −45° | −67.5° |
| 5 g | 1.7 kHz | 22.5° | 22.5° |
| 10 g | 1.4 kHz | −45° | −45° |
| 10 g | 1.4 kHz | −90° | 0° |

Examples of measurements of the characteristic of the variation of the receiving microphone output when the gas residual quantity is varied in different examples in which the gas residual quantity that is to be detected is close to 0 g are shown in FIG. 4, and, similarly, examples of measurements when the gas residual quantity is close to 5 g are shown in FIG. 5 and examples of measurement when the gas residual quantity is close to 10 g are shown in FIG. 6.

The method of selecting the above residual quantity detection conditions will now be described. It was found that when, first, the resonant frequency of the cassette-type gas cylinder 1 when it is set in a gas appliance such as a portable stove, etc. is determined, the position that is opposite the weld portion 2a of the can body 2 of the gas cylinder 1 in FIG. 3 and is displaced 180° therefrom is taken as the base point 0°, the transmitter 11 (transmitting speaker) and the receiver 12 (receiving microphone) are set in various positions which are in the range of 90°, on the left and right respectively, from this base point, and which, in this example are shifted 22.5° at a time, and the gas cylinder 1 is excited by transmission from the transmitter 11, with the frequency varied, there is a resonant frequency at 4 points in the vicinity of 1.4 kHz, 1.7 kHz, 2.2 kHz and 3.7 kHz. The strength of the reception output signals varies depending on the positions of the transmitter 11 and receiver 12, but there is resonance at common frequencies regardless of what these positions are.

The above resonant frequencies change because of the effects of errors in the shape of the cassette-type gas cylinder 1 and its strength and the effects of the room temperature, etc., and, in actual conditions, since there is an error of about ±0.1 kHz, these frequencies occur in the ranges 1.3–1.5 kHz, 1.6–1.8 kHz, 2.1–2.3 kHz and 3.6–3.8 kHz, and the resonant frequencies set for the transmitter 11 or the receiver 12 in correspondence to the above frequencies also have values in these ranges.

Figure 7A:
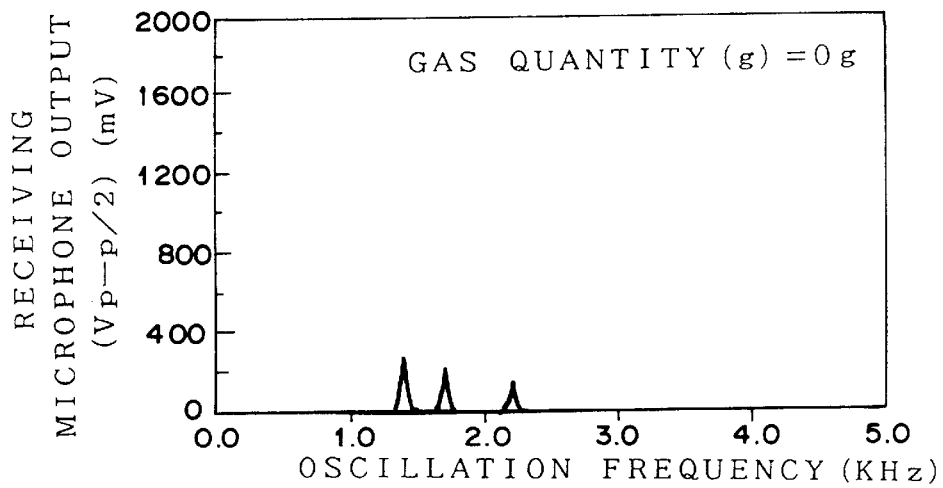
FIGS. 7A–7C shows graphs of examples of measurement of resonant frequency in correspondence to changes in gas quantities.
Figure 7B:
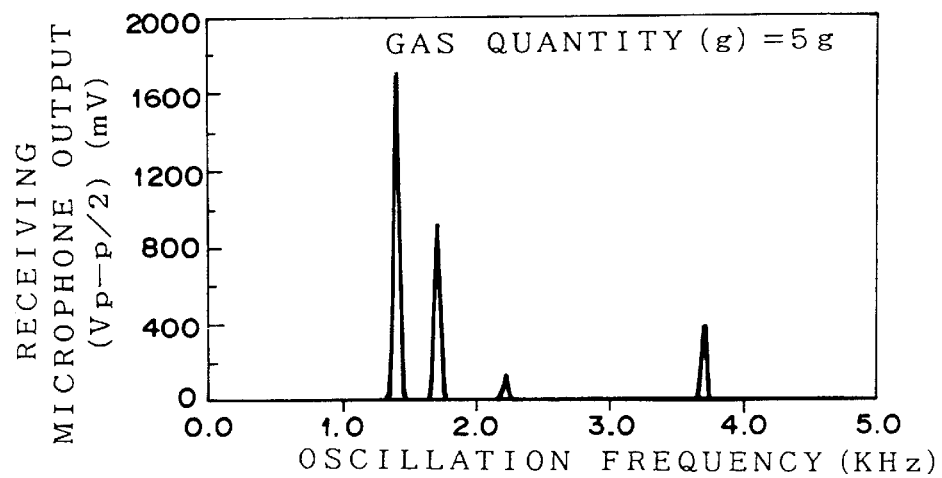
Figure 7C:
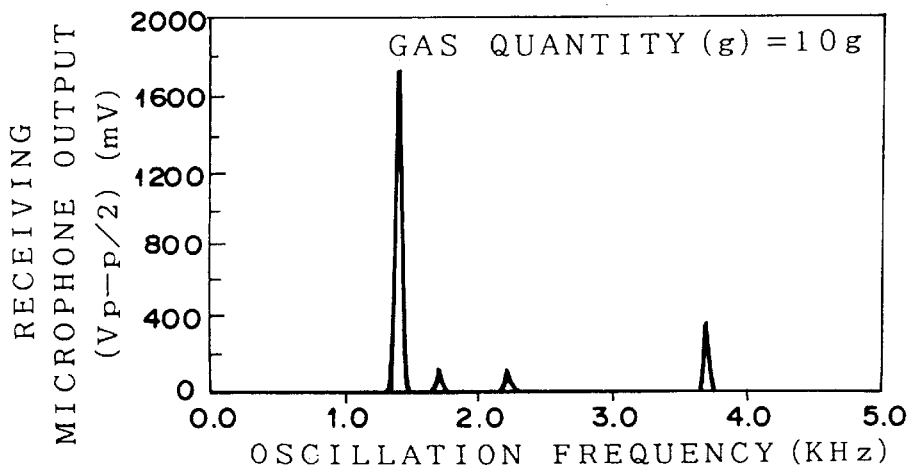
Figure 8A:
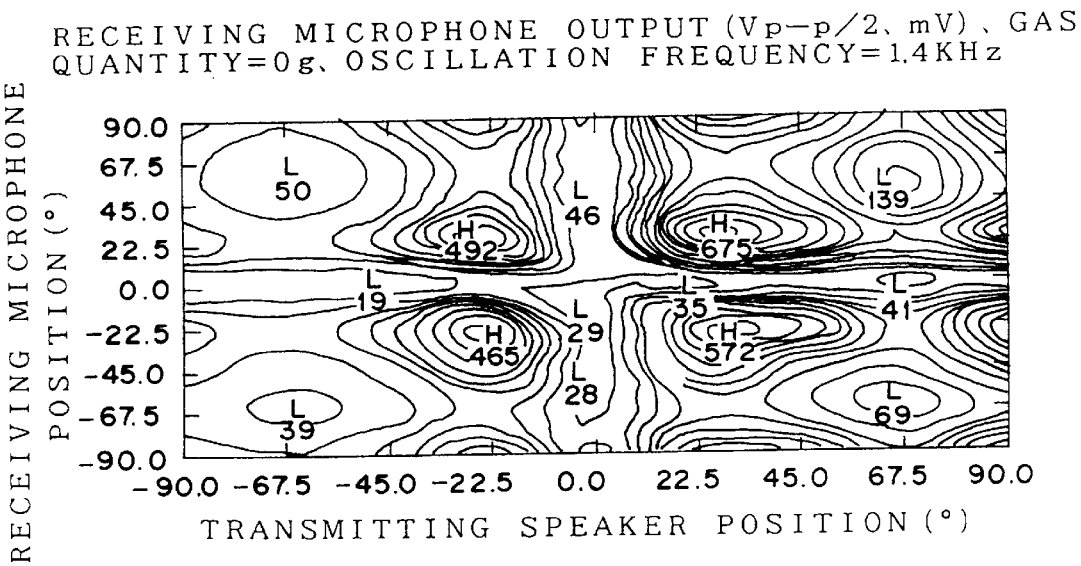
FIGS. 8A–10D are contour plots showing the findings of measurements of receiving microphone outputs in correspondence to changes in the amount of gas when the transmitting speaker position and receiving microphone position were changed.
Figure 8B:
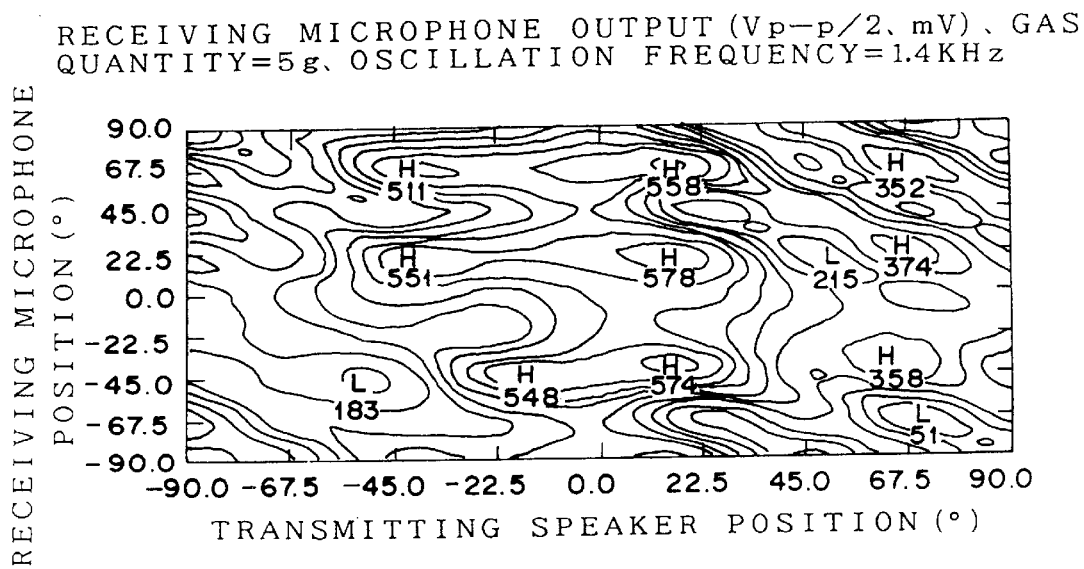
Figure 8C:
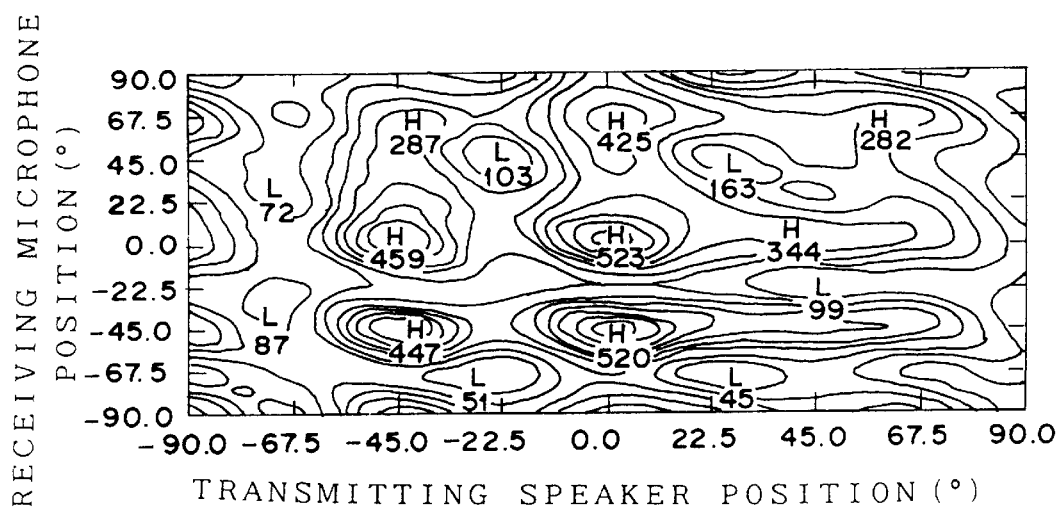
Figure 8D:
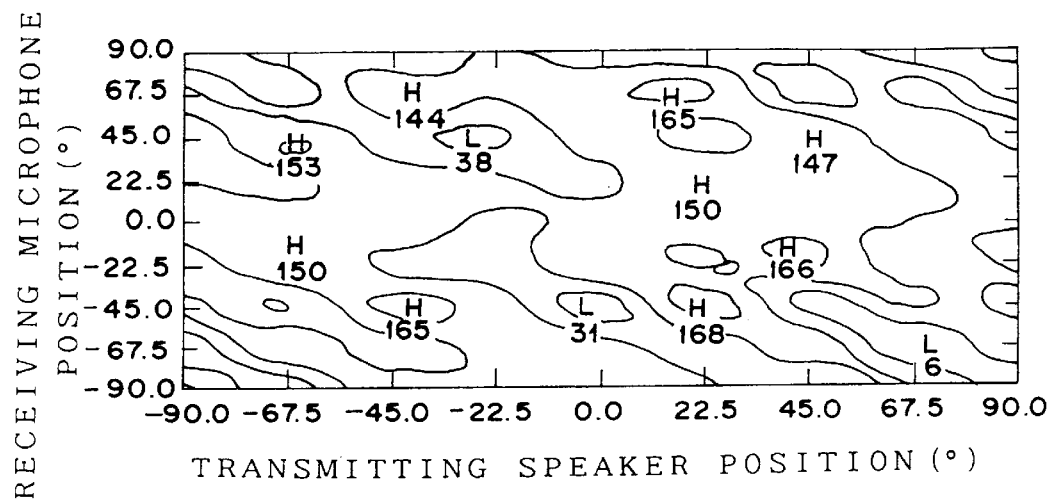
Figure 9A:
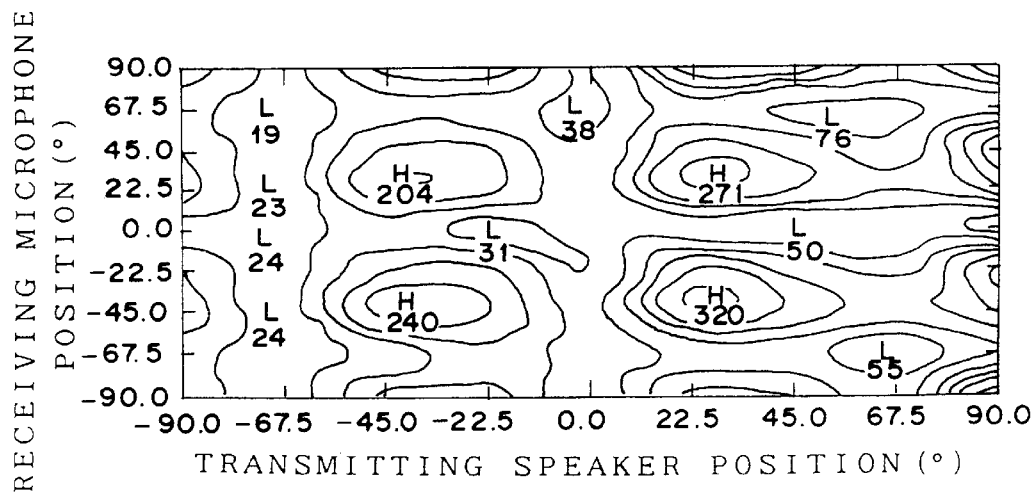
Figure 9B:
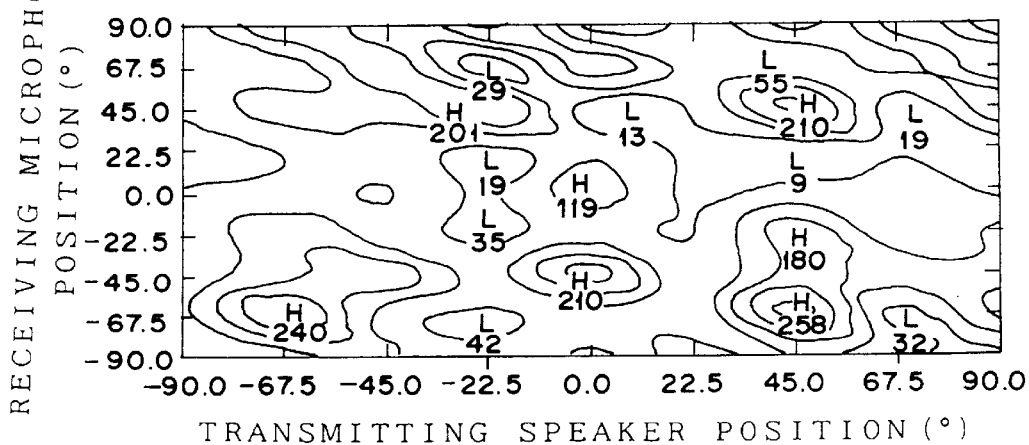
Figure 9C:
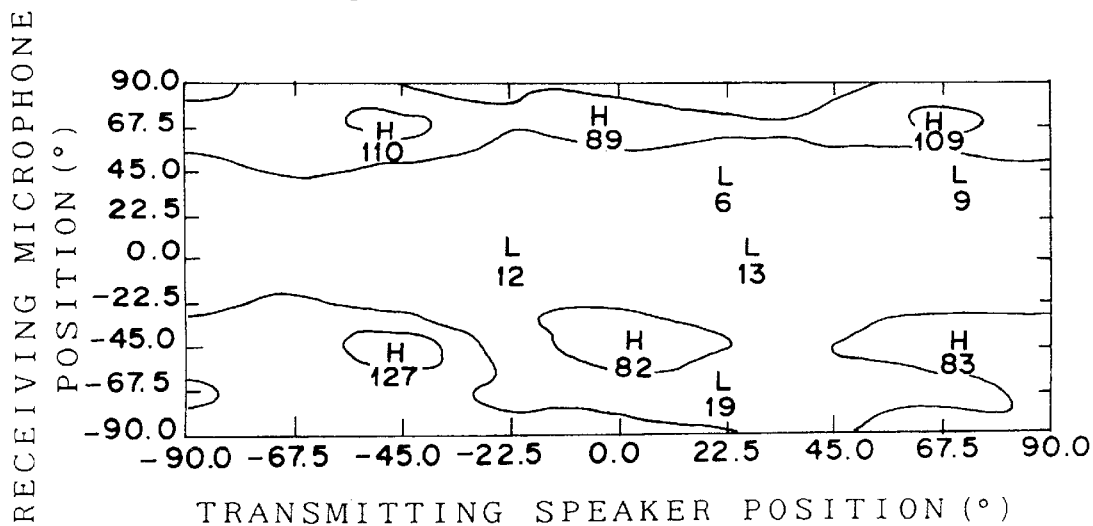
Figure 9D:
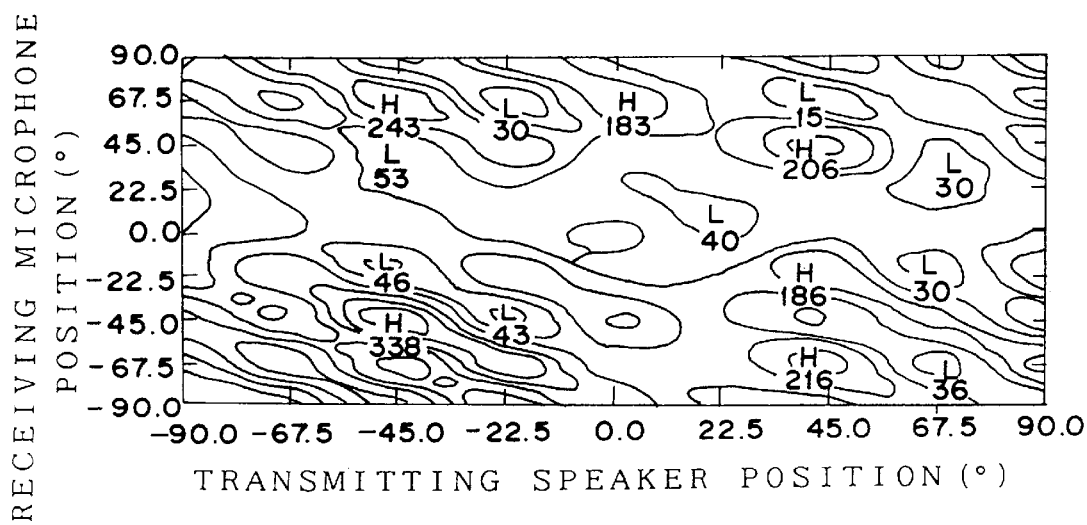
Figure 10A:
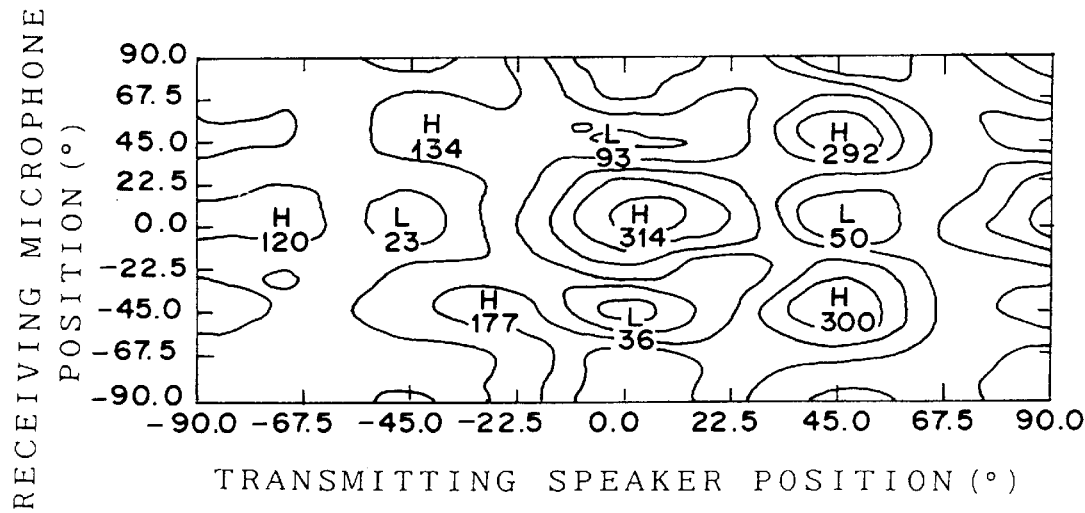
Figure 10B:
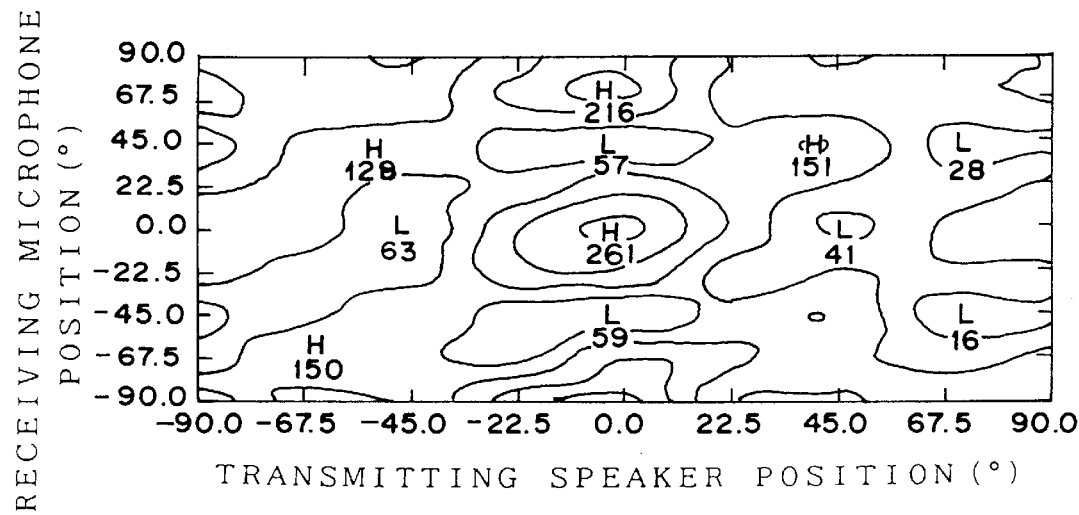
Figure 10C:
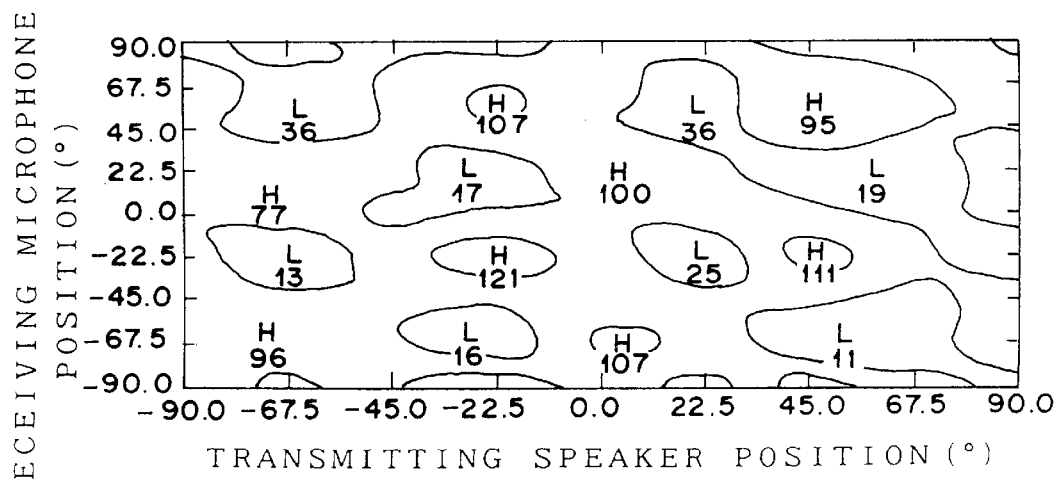
Figure 10D:
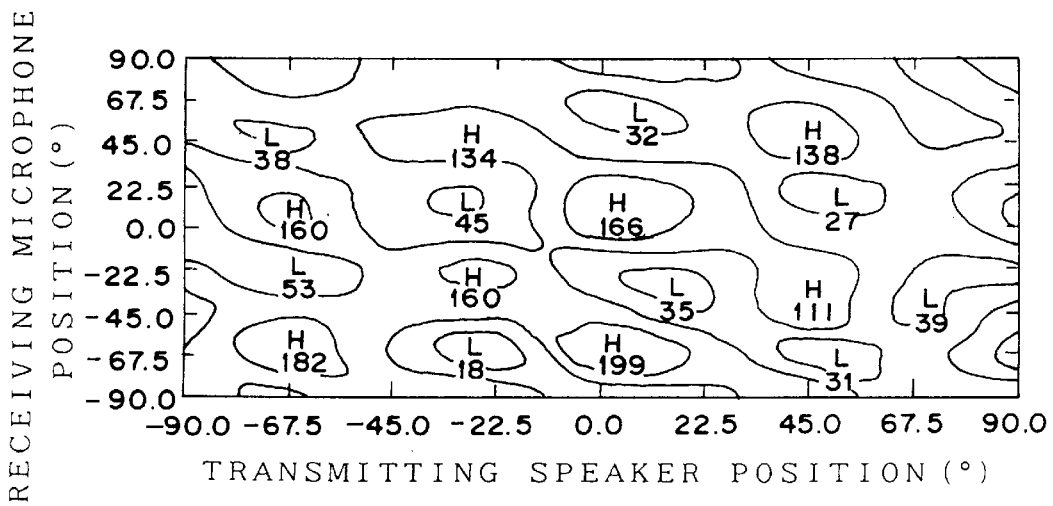

When the variation of the resonant frequency with the residual quantity of liquefied gas in the gas cylinder 1 was measured, it was found that, as shown in FIGS. 7 (A)–(B), the frequency was constant, regardless of the amount of liquefied gas, but the magnitude of the output signal changed. In other words, although the value of the resonant frequency of a container with a simple shape varies in accordance with the amount of liquid that is contained and the residual quantity can be detected by determining the frequency at which there is resonance, in the case of a cassette-type gas cylinder 1, the frequency at which there is resonance does not change with changes in the gas residual quantity, and so it is not possible to detect the amount of liquid simply by determining the frequency.

FIGS. 8 (A)–(D) show, as contour plots, the results when the positions of the transmitter 11 and receiver 12 are varied in the manner described above, transmission from the transmitter is effected at a frequency of, eg, 1.4 kHz or detection of the 1.4 kHz frequency component is effected at the receiver 12 and the receiving microphone outputs when the liquefied gas residual quantity was varied were measured. FIG. 8 (A) applies when the gas residual quantity is 0 g, FIG. 8 (B) when it is 5 g, FIG. 8 (C) when it is 10 g, and FIG. 8 (D) when it is 20 g. H in the plots indicates reception output high points, and L indicates low points.

Similarly, FIGS. 9 (A)–(D) show the results when the resonant frequency is 1.7 kHz and FIGS. 10 (A)–(D) show the results when the resonant frequency is 2.2 kHz. Illustration of the case in which the gas cylinder is 3.7 kHz is omitted.

As seen from FIGS. 8A–10D, when the liquefied gas residual quantity is 0 g, the can body 2 vibrates symmetrically centring on the base point 0°, i.e., the position opposite the weld portion 2a, but when there is a residual quantity of gas, since the weld is fixed at a position that is displaced about 20° from the vertical and the surface of the liquefied gas is horizontal, the gas cylinder 1 vibrates in a mode in which the symmetry is disordered because of this liquid surface.

Going on the basis of the findings of FIGS. 8 (A)–(D), if, in the case where the resonant frequency is 1.4 kHz, the liquefied gas residual quantity is plotted on the abscissa, the receiving microphone position is plotted on the ordinate, and contour lines of the receiving microphone output for each transmitting speaker position are drawn, the changes in vibration with changes in the amount of gas become clear, examples of this being shown in FIGS. 11 (A) and (B). FIG. 11 (A) is the case where the transmitting speaker position is −45°, and FIG. 11 (B) the case where it is −67.5°. Illustrations of the situations with other transmitting speaker positions are not shown.

Similarly, going on the basis of the findings of FIGS. 9A–9D and 10A–10D, the receiving speaker outputs contours for each transmitting speaker position are plotted for the case where the resonant frequency is 1.7 kHz, the case where it is 2.2 kHz and the case where it is 3.7 kHz (not shown in the drawings).

Figure 11A:
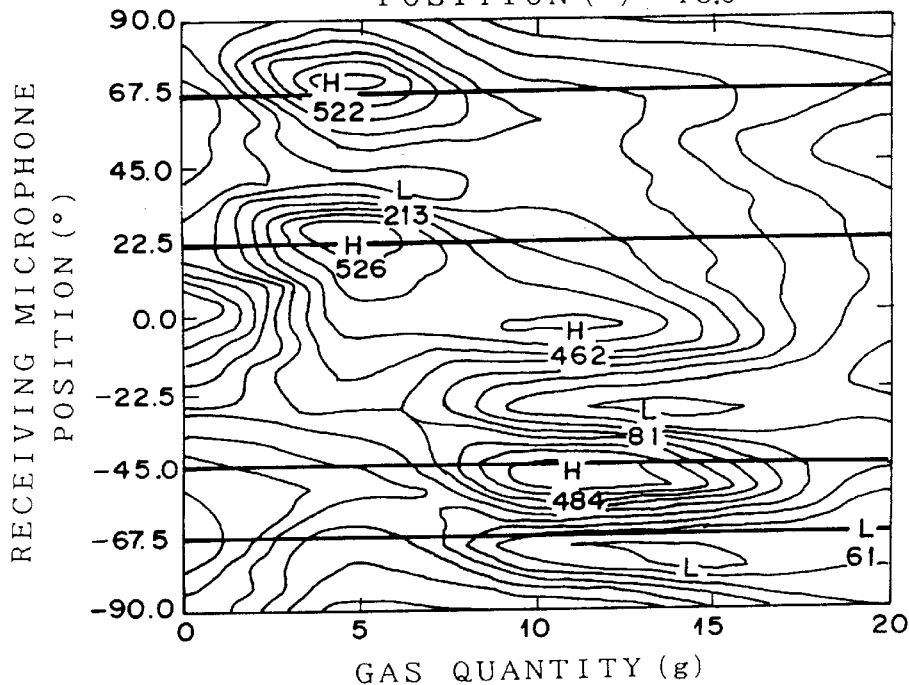
FIGS. 11A–11B shows contour plots of changes in the receiving microphone output in correspondence to changes in the receiving microphone position and the amount of gas when the transmitting speaker is in specific positions.
Figure 11B:
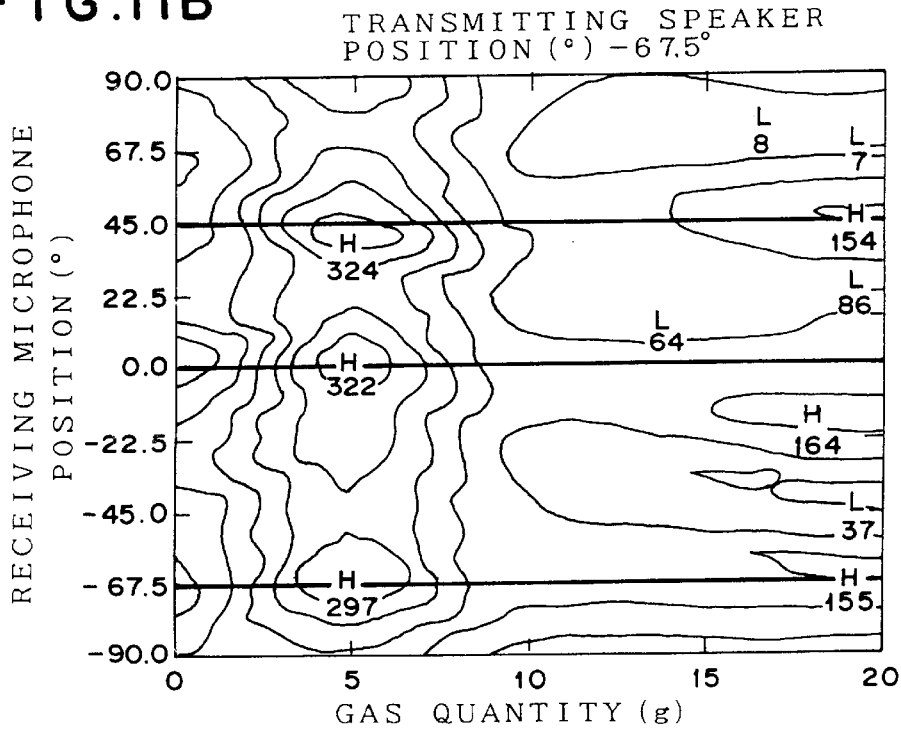

Examination of FIGS. 11A and 11B makes it possible to find conditions in which the receiving microphone output in correspondence to changes in the gas quantity displays output voltage peaks depending on the transmitting speaker and receiver microphone positions at specific gas quantities. For example, when the transmitting speaker position in FIG. 11 (A) is −45°, the region where the gas residual quantity is close to 5 g constitutes a peak and the receiving microphone positions for making the output signals low at other residual gas quantities and making the height differences large are 67.50°, 22.5° and −67.5°. When the receiving microphone position is −45°, the region where the gas residual quantity is close to 10 g becomes a peak, and the output signals at other gas residual quantities are low. When the transmitting speaker position is −67.5°, as in FIG. 11 (B), the region where the gas residual quantity is close to 5 g constitutes a peak and the receiving microphone positions with which the output signals are low and the height differences are large at other gas residual quantities are 45°, 0° and −67.5°.

Examples of selection of conditions are shown in Table 1, and when the transmitter 11 and receiver 12 are set in their specific positions in accordance with the various conditions and the characteristics of variation of the receiving microphone output with changes in the gas quantity are determined, the findings are as shown in the abovenoted FIGS. 4–6, in which the receiving microphone output voltage increases, or reaches a maximum, and exceeds a set value when the gas residual quantity is close to 0 g, 5 g and 10 g respectively. Further, if plots like those of FIGS. 8A–8D in correspondence to each resonant frequency and transmitting speaker position are similarly used to find the conditions in which the receiving microphone output increases or becomes maximum and exceeds a set value at specific gas quantities, the conditions for detection of these gas quantities can be set.

Going on the basis of the selection of detection conditions such as above, the transmission frequency of the transmitter 11 and the frequency of the bandpass filter 16 of the receiver 12 are set, the transmitter 11 and the receiver 12 are mounted in set positions, and the voltage for the start of emission of light by the light-emitting diode 20 in response to the magnitude of the reception voltage is set, so producing a configuration whereby the residual quantity is detected and an indication thereof is given when a set residual quantity is reached.

Since the dimensions, etc. of cassette-type gas cylinders 1 are specified on the basis of standards, they have generally the same vibration characteristics, even if the companies that manufacture the gas cylinders 1 are different, and so residual quantities can be detected by the same detection method.

EXAMPLE 2

Figure 12:
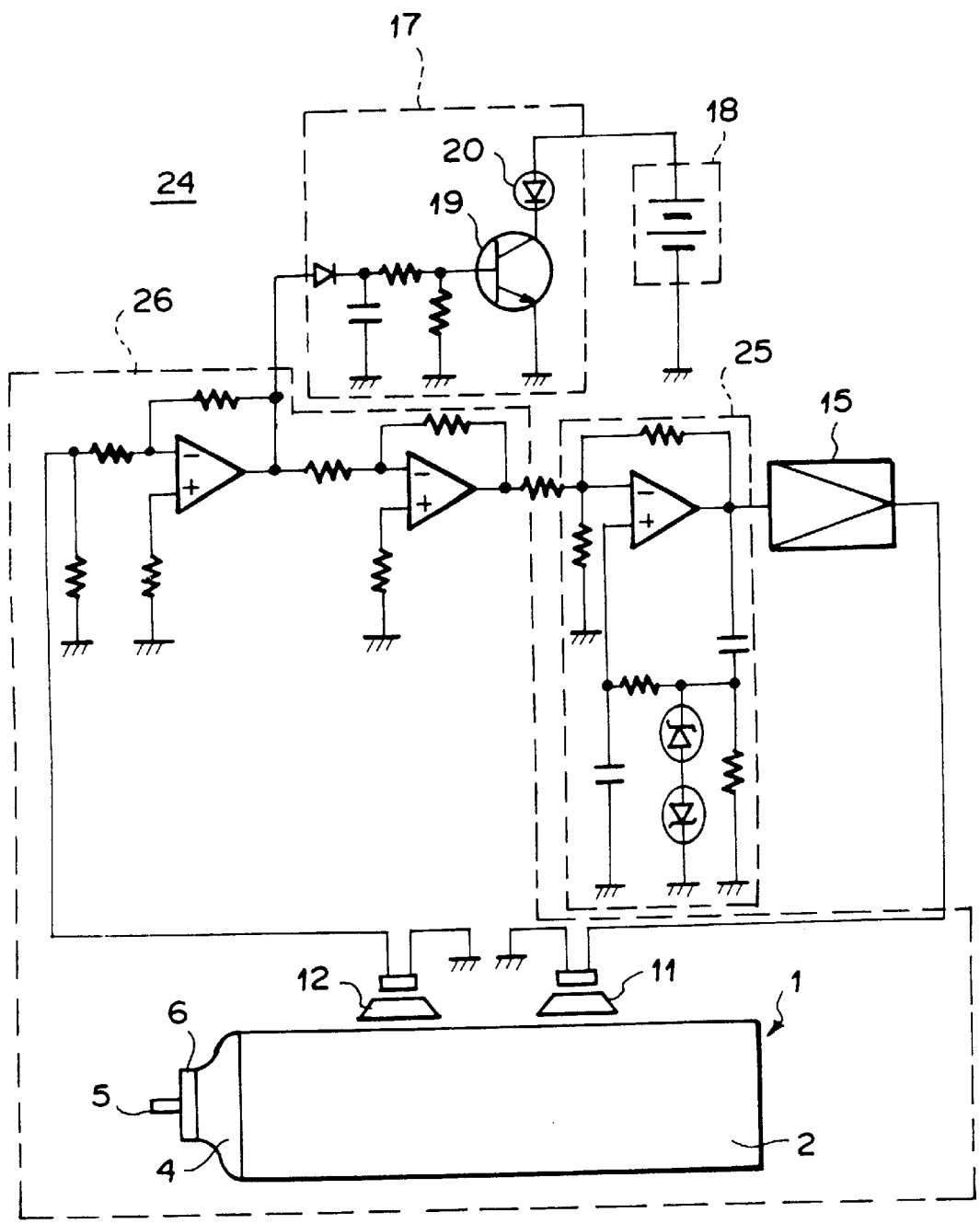
FIG. 12 is a schematic circuit diagram showing the residual quantity detection apparatus in a 2nd example of practice of the invention.

FIG. 12 shows the general configuration of the residual quantity detection apparatus of this example, and, as opposed to the separately excited detection circuit of FIG. 1, this example illustrates a self-excited detection circuit.

In the residual quantity detection apparatus 24 of this example, as in the previous example, a cassette-type gas cylinder 1 is set in a gas appliance, and a transmitter 11 (transmitting speaker) and a receiver (receiving microphone) are installed in set positions in correspondence to the liquefied gas residual quantity it is required to detect. The transmitter 11 receives input of and is driven by oscillation signals that come from a filter and phase-shift circuit 25 via an amplifier 15, and the output signals of the receiver 12 are fed back to the filter and phase-shift circuit 25 via a feedback circuit 26, so constituting a feedback-amplification circuit.

In the feedback circuit 26, during feedback of received signals, the signals are amplified, and then a portion thereof is sent to a monitor circuit 17, and the remaining signals have their level adjusted and are fed back. In the monitor circuit 17, a transistor 19 is driven and causes a light-emitting diode 20 to emit light only during oscillations, and so an indication of oscillation, ie, detection of a residual quantity is given. The frequency characteristic of the filter and phase-shift circuit 25 is set to a resonant frequency corresponding to the residual quantity that is to be detected. Transmission is started by noise components within the circuit.

As a result, when the amount of liquefied gas in the gas cylinder 1 becomes a set amount, and the reception output of the receiver 12 increases and becomes more than a set value, there is oscillation with the oscillation conditions determined by the amplification ratio and the feedback ratio are satisfied, and so oscillation occurs, and the residual quantity is detected and an indication thereof is given. Although the most efficient oscillation is produced when the input signals to the transmitter 11 for exciting the gas cylinder 1 and the output signals from the receiver 12 which detects vibration have the same phase, in practice, they do not always have the same phase, which is why the phase-shift circuit 25 is included for the purpose of phase matching. However, if the signals that are fed back are sufficiently large, oscillation can be induced even if there is no phase-shift circuit 25.

EXAMPLE 3

Figure 13:
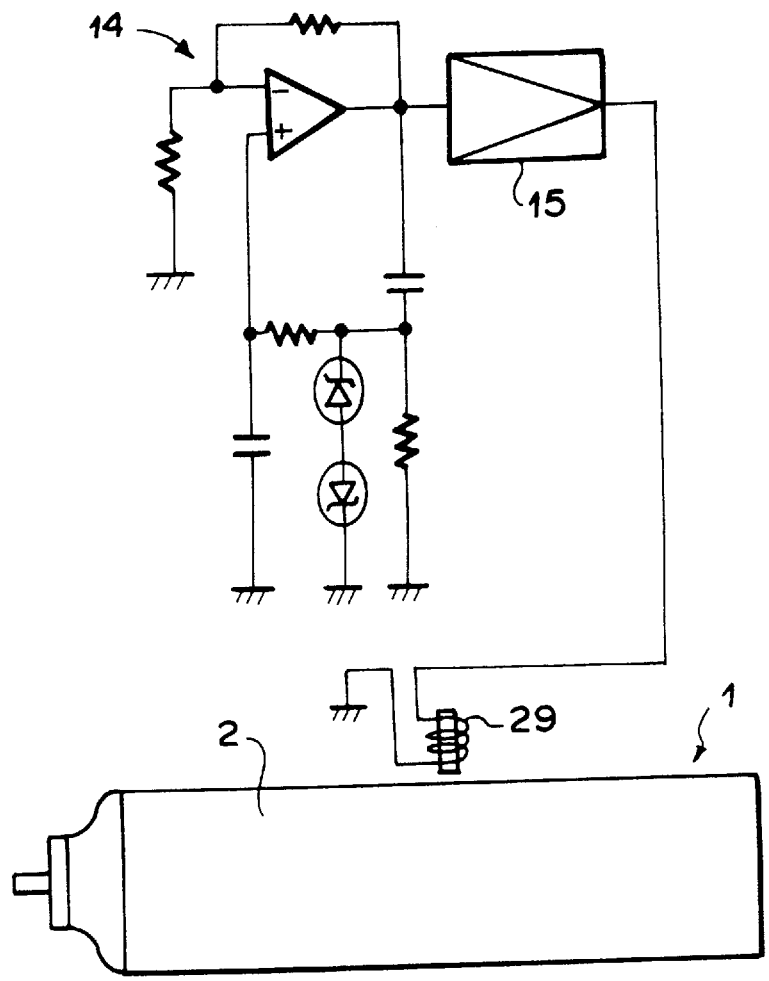
FIG. 13 is a schematic circuit diagram of a 3rd example which shows a modification of the transmitter.

This example is shown in FIG. 13, and it is an example of modification of the transmitter, in which the transmitter is constituted by a transmitting coil 29, as opposed to a transmitting speaker as in the previous examples. As far as concerns the receiver 12, this can be constituted in the same way as in Example 1, and it can be constituted by a separately excited or by a self-excited circuit.

The can body 2 of a gas cylinder 1 is formed by a steel plate (magnetic body), and it is used directly as a vibrator. The transmitting coil is positioned close to the can body 2 of the gas cylinder 1, drive signals are input from an oscillation circuit 14 into the transmitting coil 29 via an amplifier 15, and excitation drive of the can body 2 is brought about by imposition of an alternating magnetic field by the transmitting coil 29.

With the transmitter 29 of this example, a can body 2 is not caused to vibrate through the production of sound waves as is the case with the transmitters 11 of the previous examples, but a can body 2 constituted by a magnetic body is excited as a vibrator by the transmitting coil 29, and there is therefore the advantage that the detection precision is improved, since what happens is not that sound waves are transmitted from the transmitter 29 and that the receiver 12 detects vibration which is propagated directly through the air from the transmitter 29, but that only the vibration of the can body 2 is detected.

An arrangement which is particularly good in terms of no-contact excitation and prevention of incorrect operation is one which combines the transmitter constituted by the transmitting coil 29 of this example and a receiver 12 constituted by a receiving speaker as in the previous examples.

The structure of the above described transmitter 29 using a coil can be used without modification as the receiver, and it can be used as a receiver in the other examples, since it permits vibration of a can body 2 constituted by a magnetic body to be detected through changes in the coil signals.

EXAMPLE 4

Figure 14:
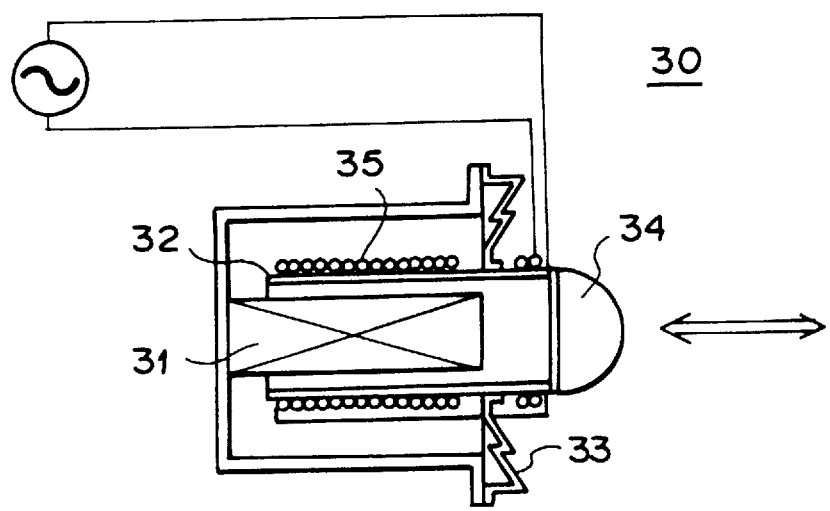
FIG. 14 is a schematic circuit diagram of a 4th example which shows a modification of the transmitter.

This example is shown in FIG. 14, and it is one in which a transmitter 30 is constituted by an electromagnetic drive vibrator. In this transmitter 30, a movable member 32 is provided around a magnet 31 in a manner such that it can be displaced by a flexible member 33. A vibration contact 34 is provided at the front end of the movable member 33, and a drive coil 35 is provided around the movable member 33, and hence around the magnet 31. This drive coil 35 is connected in a manner permitting input of alternating signals (oscillation signals).

The structure is one with which the front end of the vibration contact 34 is brought into contact with the can body 2 of a gas cylinder 1, and the can body 2 is excited by direct imposition of vibration.

The structure of this electromagnetic drive vibrator is one in which an electromagnet is used to excite a vibrator, and a conventionally known structure can be suitably employed for this structure. Further, a device using a piezoelectric element, etc. can be suitably employed as a drive element such as this.

Also, the structure of this transmitter 30 constituted by a vibrator can be used directly as a receiver in the form of a pickup, and it is one which permits the vibration of a vibrator contacting the can body 2 to be detected by an electromagnetic or piezoelectric element, etc., and which can also be used for the receiver in the other examples.

EXAMPLE 5

Figure 15:
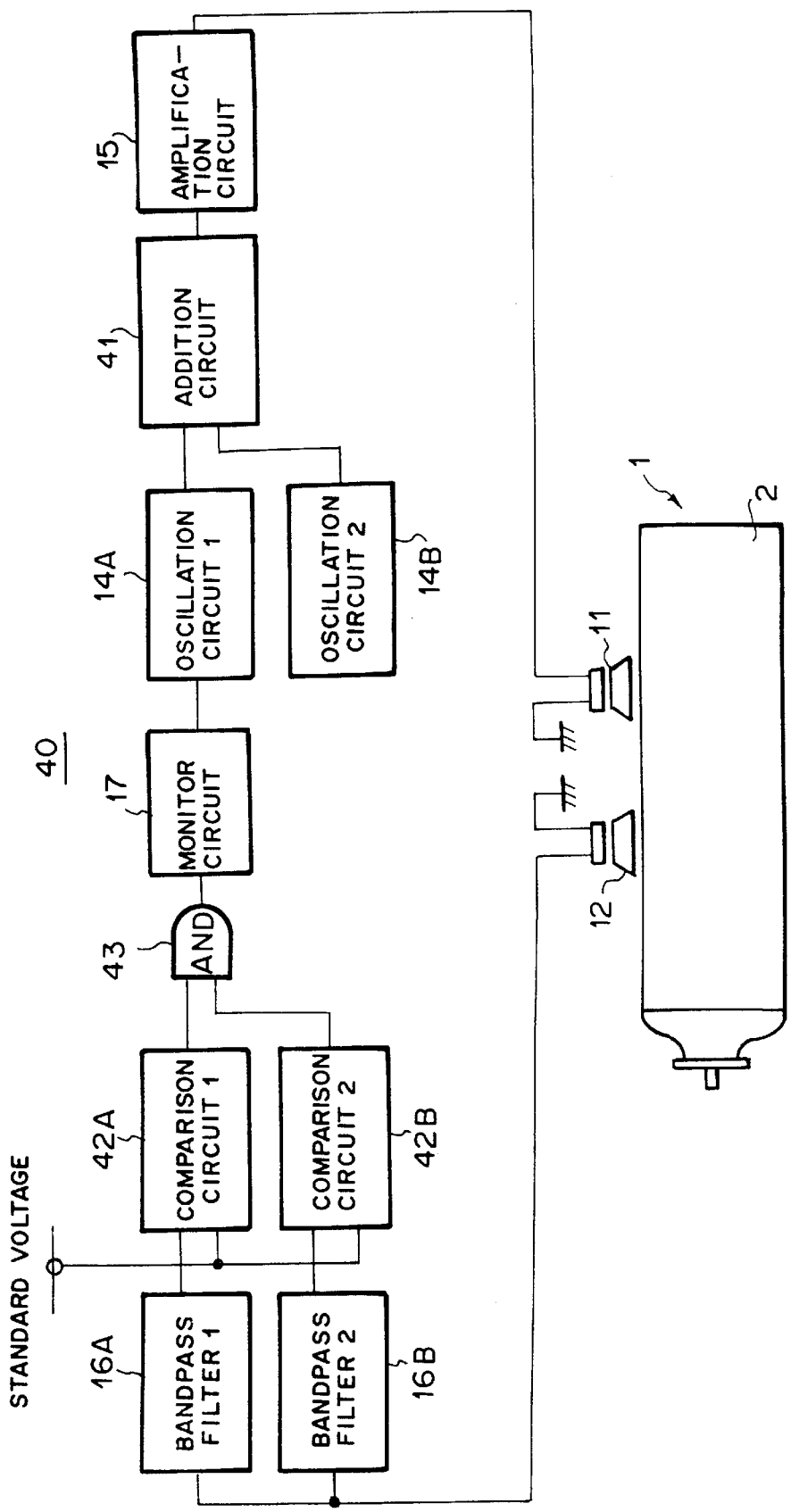
FIG. 15 is a schematic block diagram of the residual quantity detection apparatus in a 5th example.

The basic configuration of the residual quantity detection apparatus 40 of this example illustrates an example in which, as shown in FIG. 15, residual quantity detection is effected by driving a transmitter 11 with oscillation signals in which two resonant frequencies are superimposed.

The transmitter 11 and receiver 12 of the residual quantity detection apparatus 40 are positioned relative to the can body 2 of a gas cylinder 1 in the same way as in Example 1. The oscillation signals of 1st and 2nd oscillation circuits 14A and 14B which output oscillation signals of different frequencies are superimposed and added by an adder circuit 41 and are input into the receiver 12 via an amplification circuit 15 and drive it, and the gas cylinder 1 is excited by two resonant frequencies.

The output signals of the receiver 12 are sent to the 1st and 2nd bandpass filters 16A and 16B of two types corresponding to the two oscillation frequencies, their frequency components are compared with reference values in respective 1st and 2nd comparison circuits 42A and 42B, and, if there is resonance output greater than the reference value in either of the frequency components, a signal from an AND circuit 43 is output to a monitor circuit 17, so effecting detection and indication of a residual quantity.

Figure 16:
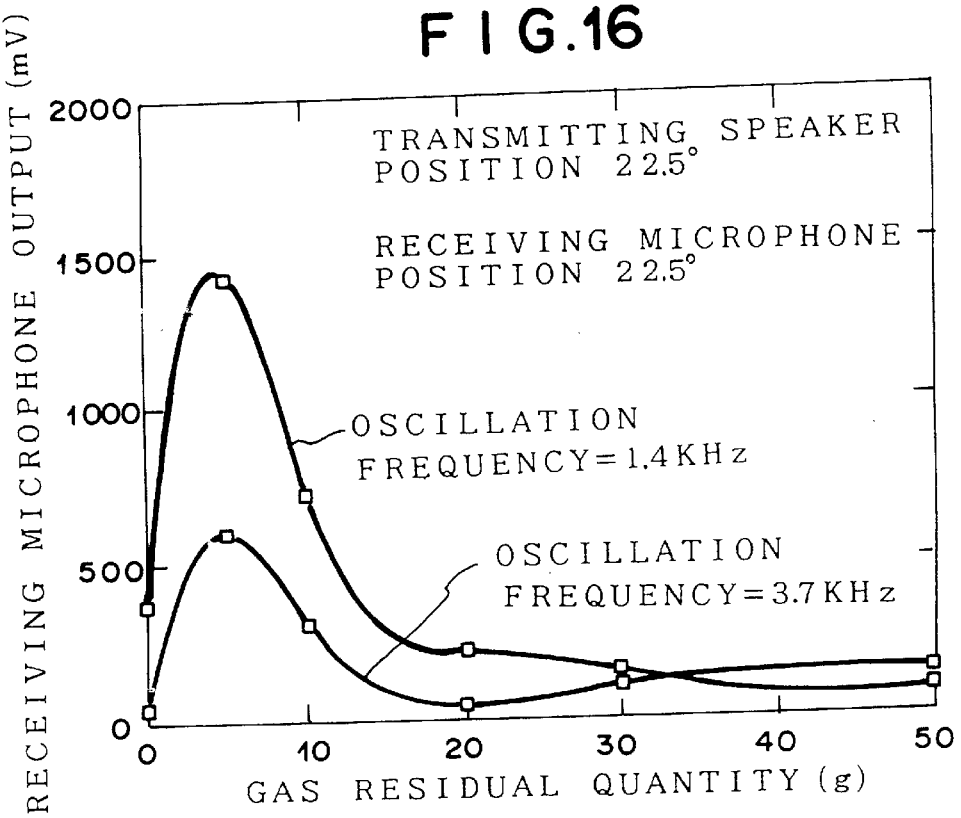
FIG. 16 is a graph showing examples of the detection characteristic of FIG. 15.

The transmitter 11 and receiver 12 are installed in positions (22.5° for both) such that, as indicated in FIG. 16, at both the resonant frequencies (1.4 kHz and 3.7 kHz), the reception output becomes maximum and exceeds a set value at the same gas residual quantity (5 g), in response to changes in the residual quantity of gas in the gas cylinder 1, and reference values are set as detection levels in the comparison circuits 42A and 42B in correspondence to the magnitudes of the reception outputs for the respective frequency components.

When, as shown in the detection characteristics of FIG. 4, the transmitting speaker is installed at 90° and the receiving microphone at −90°, the setting may similarly be made such that two frequencies are added, since a gas residual quantity close to 0 g can be detected both when the resonant frequency is 1.4 kHz and when it is 1.7 kHz.

In this-example, since detection when a set gas residual quantity is reached is effected on the basis of the output signals of two resonant frequencies, the reliability of the detection operation is better than it is in detection using a single resonant frequency. That is, setting two resonant frequencies makes it possible to prevent incorrect detection operation at gas residual quantities other than the set value due to the reception output of the receiver 12 increasing because, depending on the ambient environment in which the gas appliance is located, the gas cylinder 1 is excited by vibration propagated by an external vibration source, or, because of the effects of noise, a set single resonant frequency and the noise frequency are close to one another.

EXAMPLE 6

Figure 17:
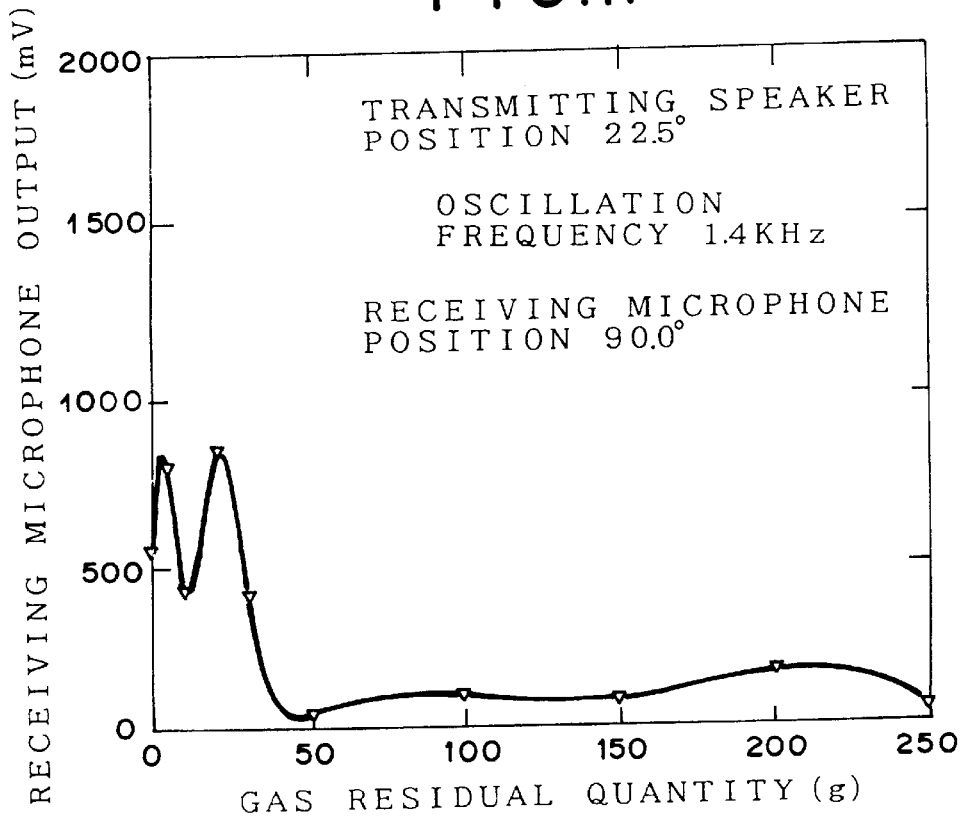
FIG. 17 is a graph showing an example of the detection characteristic in a 6th example.

The residual quantity detection apparatus of this example is similar to that of Example 1, and its detection characteristic is shown in FIG. 17.

The residual quantity detection characteristic in this example is such that the reception output increases and residual quantity detection is effected at plural gas residual quantities. FIG. 17 shows the case where residual quantity detection is effected when the gas residual quantity is 5 g and when it is 20 g, and the resonant frequencies and the transmitter 11 and receiver 12 installation positions are so selected that this detection characteristic is produced. As a result, detection and indication of residual gas quantities can be effected in two stages.

What is claimed is:

1. A cassette-type gas cylinder residual quantity detection method in which a gas cylinder containing liquefied gas is set in a gas appliance and a transmitter which excites said gas cylinder and a receiver which detects vibration of said gas cylinder are installed in positions for each of which the position that is opposite a weld portion of a can body of said gas cylinder is taken as a reference, and at which, when there is a specific resonant frequency and a residual gas quantity it is intended to detect, the reception output of said receiver becomes greater than, a set value, the method comprising:

transmitting signals of said specific resonant frequency, from the transmitter; and detecting when the reception output of said receiver becomes more than said set value as indicating that the amount of liquefied gas in said gas cylinder is said residual gas quantity.

2. A cassette-type gas cylinder residual quantity detection method as claimed in claim 1 further comprising:

setting a cassette-type gas cylinder containing liquefied gas in a gas appliance, installing said transmitter which excites said gas cylinder and said receiver which detects vibration of said gas cylinder near said can body of said gas cylinder, varying the frequency of excitation signals transmitted by said transmitter;

determining the resonant frequencies that are produced in said gas cylinder without relation to the amount of liquefied gas in said gas cylinder, and using said position which is opposite said weld portion of said can body of said gas cylinder as a reference, determining the relations of the transmitter and receiver dispositions and the reception outputs in respect of the amount of liquefied gas in the gas cylinder at said resonant frequencies, and determining from these relations the installation positions of said transmitter and receiver at which, when there is a specific residual amount of gas which it is wished to detect, the reception output produced by the receiver becomes more than a set value.

3. A cassette-type gas cylinder residual quantity detection method as claimed in claim 1, wherein the frequency of the excitation signals produced by said transmitter is set at 1.3–1.5 kHz, 1.6–1.8 kHz, 2.1–2.3 kHz or 3.6–3.8 kHz.

4. A cassette-type gas cylinder residual quantity detection method as claimed in claim 1, including transmitting from the transmitter signals in which there is superimposed addition of plural resonant frequencies at which the reception output becomes more than a set value when there is a specific residual gas quantity, and detecting that the amount of liquefied gas is said specific residual gas quantity when the reception output becomes greater than the set value at each of said resonant frequencies.

5. A cassette-type gas cylinder residual quantity detection method as claimed in claim 1, including setting a plurality of transmitter and receiver installation positions providing resonant frequencies with the characteristics that the reception output increases at plural residual gas quantities, and detecting plural residual gas quantities.

6. A cassette-type gas cylinder residual quantity detection apparatus comprising:

a cassette-type gas cylinder having a can body with a weld portion containing liquefied gas set in a gas appliance, a transmitter which excites said gas cylinder and a receiver which detects gas cylinder vibration installed near the can body of said gas cylinder in positions for each of which the position that is opposite the weld portion of said can body is taken as a reference, and at which the reception output of said receiver becomes greater than a set value when there is a specific resonant frequency and a residual gas quantity it is wished to detect, an oscillation circuit which produces signals of a specific resonant frequency connected to said transmitter, and a monitor circuit connected to the receiver which detects when the reception output at said reception frequency is greater than said set value.

7. A cassette-type gas cylinder residual quantity detection apparatus comprising a cassette-type gas cylinder having a can body with a weld portion containing liquefied gas set in a gas appliance, a transmitter which excites said gas cylinder and a receiver which detects gas cylinder vibration installed near the can body of said gas cylinder in positions for each of which the position that is opposite the weld portion of said can body is taken as a reference, and at which the reception output of said receiver becomes greater than a set value when there is a specific resonant frequency and a residual gas quantity it is wished to detect, an oscillation circuit which produces signals of a specific resonant frequency connected to said transmitter, a monitor circuit connected to the receiver which detects when the reception output at said reception frequency is greater than said set value, and a feedback circuit which feeds back a portion of said resonant frequency reception signals to said transmission circuit.

8. A cassette-type gas cylinder residual quantity detection apparatus as claimed in claim 6 or claim 7, wherein said transmitter is a transmitting speaker and excites said gas cylinder with sound pressure.

9. A cassette-type gas cylinder residual quantity detection apparatus as claimed in claim 6 or claim 7, wherein said transmitter is selected from an electromagnetic drive vibrator and a piezoelectric element, whose vibration excites said can body.

10. A cassette-type gas cylinder residual quantity detection apparatus as claimed in claim 6 or claim 7, wherein said receiver is a receiving microphone.

11. A cassette-type gas cylinder residual quantity detection apparatus as claimed in claim 6 or claim 7, wherein said receiver is a receiving coil.

12. A cassette-type gas cylinder residual quantity detection apparatus as claimed in claim 6 or claim 7, wherein said receiver is a pickup selected from an electromagnetic and a piezoelectric element.

13. A cassette-type gas cylinder residual quantity detection apparatus as claimed in claim 6 or claim 7, wherein said transmitter is constituted by a transmitting coil, and said receiver is constituted by a receiving microphone.

14. A cassette-type gas cylinder residual quantity detection apparatus comprising:

a cassette-type gas cylinder having a can body with a weld portion containing liquefied gas set in a gas appliance, a transmitter which excites said gas cylinder and a receiver which detects gas cylinder vibration installed near the can body of said gas cylinder in positions for each of which the position that is opposite the weld portion of said can body is taken as a reference, and at which the reception output of said receiver becomes greater than a set value when there is a specific resonant frequency and a residual gas quantity it is wished to detect, an oscillation circuit which produces signals of a specific resonant frequency connected to said transmitter, and a monitor circuit connected to the receiver which detects when the reception output at said reception frequency is greater than said set value, wherein said transmitter is a transmitting coil and the gas cylinder can body is a magnetic body excited by imposition of an alternating magnetic field thereon.

15. A cassette-type gas cylinder residual quantity detection apparatus comprising:

a cassette-type gas cylinder having a can body with a weld portion containing liquefied gas set in a gas appliance, a transmitter which excites said gas cylinder and a receiver which detects gas cylinder vibration installed near the can body of said gas cylinder in positions for each of which the position that is opposite the weld portion of said can body is taken as a reference, and at which the reception output of said receiver becomes greater than a set value when there is a specific resonant frequency and a residual gas quantity it is wished to detect, an oscillation circuit which produces signals of a specific resonant frequency connected to said transmitter, and a monitor circuit which connected to the receiver which detects when the reception output at said reception frequency is greater than said set value and a feedback circuit which feeds back a portion of said resonant frequency reception signals to said transmission circuit, wherein said transmitter is a transmitting coil and the gas cylinder is a magnetic body excited by imposition of an alternating magnetic field thereon.

* * * * *